US008832139B2

(12) United States Patent
Selly

(10) Patent No.: US 8,832,139 B2
(45) Date of Patent: Sep. 9, 2014

(54) ASSOCIATIVE MEMORY AND DATA SEARCHING SYSTEM AND METHOD

(76) Inventor: Roger Selly, Palo Alto, CA (US)

(*) Notice: Subject to any disclaimer, the term of this patent is extended or adjusted under 35 U.S.C. 154(b) by 18 days.

(21) Appl. No.: 11/914,554

(22) PCT Filed: May 15, 2006

(86) PCT No.: PCT/US2006/018699
§ 371 (c)(1),
(2), (4) Date: Nov. 15, 2007

(87) PCT Pub. No.: WO2006/124760
PCT Pub. Date: Nov. 23, 2006

(65) Prior Publication Data
US 2009/0307218 A1    Dec. 10, 2009

Related U.S. Application Data

(60) Provisional application No. 60/681,374, filed on May 16, 2005.

(51) Int. Cl.
*G06F 17/30* (2006.01)
*G06F 7/00* (2006.01)

(52) U.S. Cl.
USPC ........... 707/769; 707/722; 707/741; 707/756; 707/758; 707/764; 382/129

(58) Field of Classification Search
None
See application file for complete search history.

(56) References Cited

U.S. PATENT DOCUMENTS

| | | | | |
|---|---|---|---|---|
| 5,161,204 A | * | 11/1992 | Hutcheson et al. | 382/157 |
| 5,706,498 A | * | 1/1998 | Fujimiya et al. | 702/20 |
| 6,054,268 A | | 4/2000 | Perlin | |
| 6,317,766 B1 | * | 11/2001 | Grover | 708/400 |
| 6,321,182 B1 | * | 11/2001 | Suzuki | 703/14 |
| 6,466,923 B1 | * | 10/2002 | Young | 706/13 |
| 6,551,784 B2 | * | 4/2003 | Fodor et al. | 506/9 |
| 6,578,018 B1 | * | 6/2003 | Ulyanov | 706/14 |
| 2002/0152191 A1 | * | 10/2002 | Hollenberg et al. | 707/1 |
| 2003/0228591 A1 | * | 12/2003 | Scafe et al. | 435/6 |
| 2004/0193789 A1 | * | 9/2004 | Rudolf | 711/108 |

FOREIGN PATENT DOCUMENTS

| | | |
|---|---|---|
| JP | 2003141538 A | 5/2003 |
| JP | 2005078407 A | 3/2005 |

OTHER PUBLICATIONS

A.A. Ezhov "Quantum Associative Memory with Distributive Queries", Information Sciences, Jul. 4, 2000, pp. 271-293.*

(Continued)

*Primary Examiner* — Jung Kim
*Assistant Examiner* — James J Wilcox
(74) *Attorney, Agent, or Firm* — Morgan, Lewis & Bockius LLP

(57) ABSTRACT

A method for searching a database (206) with stored information using parallel searching of superposition representations of the information. In one approach, the method involves searching a target DNA or RNA genome (16) sequence to determine whether a match is present between a sequence probe and the target. The method includes encoding the target sequence as superpositions of wavefunctions, encoding the probe as one or more wavefunctions, and comparing the encoded target with the encoded probe. The encoding of the target may involve applying a transform (e.g., discrete Fourier transform) to the target sequence to obtain the wavefunctions used to form the one or more superposition representations.

10 Claims, 10 Drawing Sheets

(56) References Cited

OTHER PUBLICATIONS

Ahsen, Nicholas von, et al. "Application of a Thermodynamic Nearest-Neighbor Model to Estimate Nucleic Acid Stability and Optimize Probe Design: Prediction of Melting Points of Multiple Mutations of Apolipoprotein B-3500 and Factor V with a Hybridization Probe Genotyping Assay on the LightCycler", Clinical Chemistry, pp. 1-13, 1999.*

European Supplementary Search Report; EP 06075 9826; pp. 1-3.

Ezhov, A. A; et al.; "Quantum Associative Memory with Distributed Queries"; Information Sciences 128; [Online] 2000; pp. 271-293; XP002543982; Retrieved from the Internet: URL: http://www.sciencedirect.com/science; the whole document.

Grover, Lov K.; "A Fast Quantum Mechanical Algorithm for Database Search"; [On-line]; Nov. 19, 1996; XP002543984; Retrieved from the Internet: URL: http://arxiv.org/PS_cache/quant-ph/pdf/9605/9605043v3.pdf>; Retrieved on Sep. 2, 2009.

International Search Report PCT/US2006/018699 dated Oct. 23, 2007; pp. 1-2.

Trugenberger, C.A.; "Quantum Pattern Recognition"; Quantum Information Processing Kluwer Academic/Plenum Publishers Netherlands; vol. 1; No. 6; Dec. 2002; pp. 471-493; XP002543983; ISSN: 1570-0755; the whole document.

Ventura, et al.; "Quantum Associative Memory"; Information Sciences Elsevier USA; vol. 124; No. 1-4; May 2000; pp. 273-296; XP002543981; ISSN: 0020-0255; the whole document.

Ventura, et al.; "Quantum Associative Memory with Exponential Capacity"; Neural Networks Proceedings, 1988; IEEE World Congress on Computational Intelligence; The 1998 IEEE International Joint Conference on Anchorage, AK, USA May 4-9, 1998; New York; USA; IEEE; US vol. 1; May 4, 1998; pp. 509-513; XP010286557; ISBN: 978-0-7803-4859-2; the whole document.

* cited by examiner

FIG. 6

| Layer Encoding Index | 0 (64 deep) | 1 (32 deep) | 2 (16 deep) | 5 (2 deep) | 6 (1 deep) |
|---|---|---|---|---|---|
| 0 | $s_0 s_1$ | $s_0 s_1 s_2 s_3$ | $s_0 \ldots s_7$ | $s_0 \ldots s_{63}$ | $s_0 \ldots s_{127}$ |
| 1 | $s_2 s_3$ | $s_4 s_5 s_6 s_7$ | $s_8 \ldots s_{15}$ | $s_{64} \ldots s_{127}$ | |
| 2 | $s_4 s_5$ | $s_8 s_9 s_{10} s_{11}$ | $\vdots$ | | |
| $\vdots$ | | $\vdots$ | $\vdots$ | | |
| 31 | | $s_{124} s_{125} s_{126} s_{127}$ | | | |
| $\vdots$ | $s_{124} s_{125}$ | | | | |
| 63 | $s_{126} s_{127}$ | | | | |

Track → 902

900

904

ASSOCIATIVE MEMORY AND DATA SEARCHING SYSTEM AND METHOD

RELATED APPLICATION

This application is a non-provisional application claiming benefit under 35 U.S.C. sec. 119(e) of U.S. Provisional Application Ser. No. 60/681,374, filed May 16, 2005 (titled Associative Memory and Data Searching System and Method by Roger Selly), which is hereby incorporated in full by reference herein.

FIELD

The present disclosure generally relates to a method and system for storing and searching large data sets, and more particularly to a method and system for searching data to locate a match to a query and/or to assess a degree of similarity of a query to information stored in the database. One specific embodiment disclosed herein relates to a method and system for searching a database of target DNA or RNA sequences for a probe sequence that matches or closely resembles a given DNA or RNA sequence that is located in the target DNA or RNA sequences.

BACKGROUND

The function of an associative memory is commonly used to detect cache "hits" in a computer system by comparing an address word with a memory of address words previously accessed. A "hit" occurs when there are a match between the input address word and an entry in this database. The output of this hit is the cache line where the address was previously read into. An associative memory is therefore in essence a parallel recognition process where a new input is compared with the entire database of prior experiences to detect any match, and in the case of a hit, to output the reference or location.

Parallel recognition processes are conceptually simple, but in actual existing practice grow exponentially in complexity and are unfeasible except for the most limited and small database applications. One potential application of parallel recognition processes is in the searching of DNA/RNA sequences. Such an application of computers to solve information processing problems in the life sciences area is within the general field known as "bioinformatics." However, searches of DNA/RNA sequences typically involve very large databases potentially containing millions to hundreds of millions of bases. These size ranges are inconsistent with the small database sizes suitable for existing parallel recognition processes.

The bioinformatics field, which, in a broad sense, includes any use of computers in solving information problems in the life sciences, and more particularly, the creation and use of extensive electronic databases on genomes, proteomes, etc., is currently in a stage of rapid growth. In order to better appreciate some of the concepts in the bioinformatics field, it is helpful to discuss some of the basic principles of cells.

A cell relies on proteins for a variety of its functions. Producing energy, biosynthesizing all component macromolecules, maintaining cellular architecture, and acting upon intra- and extra-cellular stimuli are all protein-dependent activities. Almost every cell within an organism contains the information necessary to produce the entire repertoire of proteins that the organism can specify. This information is stored as genes within the organism's DNA genome. Different organisms have different numbers of genes to define them. The number of human genes, for example, is estimated to be approximately 25,000.

Genetic information of all life forms is encoded by four basic nucleotides (adenine, thymine, cytosine, and guanine, which are designated by the letters "A", "T", "C", and "G", respectively). The genes are grouped in the base pairs A-T and G-C, and a DNA sequence refers to the ordering or pattern of the nucleotide bases in the gene. The length of a DNA sequence can be very large, and for instance, a DNA sequence may have between 2,000 and two million base pairs. The make-up of all life forms is determined by the sequence of these nucleotides. DNA is the molecule that encodes this sequence of nucleotides.

Each gene typically provides biochemical instructions on how to construct a particular protein. In some cases multiple genes are required to create a single protein, and multiple proteins can be produced through alternative splicing and post-transcriptional modification of a single gene.

Only a portion of the genome is composed of genes, and the set of genes expressed as proteins varies between cell types. Some of the proteins present in a single cell are likely to be present in all cells because they serve functions required in every type of cell. These proteins can be thought of as "housekeeping" proteins. Other proteins serve specialized functions that are only required in particular cell types. Such proteins are generally produced only in limited types of cells. Given that a large part of a cell's specific functionality is determined by the genes that it is expressing, it is logical that transcription, the first step in the process of converting the genetic information stored in an organism's genome into protein, would be highly regulated by the control network that coordinates and directs cellular activity.

There are approximately three billion different DNA base pairs that may be found in humans, and the particular DNA sequences that each person has are located in 23 pairs of chromosomes that contain about 100,000 individual genes. It is significant that faulty genes can be linked to a large variety of human afflictions. An ability to relate an individual gene directly with a particular medical health problem can lead to predictive tests, treatments, and potential cures for a wide variety of medical problems and hereditary ailments.

Currently, about 2,000 human DNA sequences are known and identified, and these DNA sequences are stored in available databases. The number of known and identified human DNA sequences is only a small fraction of the enormous total number of human DNA sequence combinations, and the number of such known and identified DNA sequences is growing rapidly. In addition, the number of DNA sequences of other organisms that have been identified and that are available in databases is also large and likewise growing with time.

The DNA sequence information contained in these growing databases will be a major instrument for basic medical and biological research activities for many years. This information will also be a basis for developing curative techniques for medical and hereditary afflictions. In order to use effectively the information in these enormous and growing databases, it is necessary to provide an efficient means to access that information. In particular, it is necessary to provide an efficient and reliable means to compare a given DNA sequence to the library of known DNA sequences in the databases. Such a comparison is useful to identify, analyze, and interpret that given DNA sequence.

Current procedures for making such comparisons are comparatively slow and impractical. As the amount of stored information increases, current search methods will become unable to function with practical, short processing times, and these methods will have very slow operating speeds. Existing technology is not practical for searching large-scale DNA databases, which may have three billion or more base pair data items.

In addition to the above limitations in searching DNA sequence databases, another of the current limitations on drug discovery research involving the analysis of genome structure and function is the need to perform wet DNA hybridization assays because accurate "in silico" simulations are not available. Further, existing sequence matching tools, such as BLAST, often miss important sequence motifs since they lack the resolution to detect short sequences (e.g., less than 14 bases in length).

Accordingly, it would be desirable to have an improved solution that overcomes the exponentially growing complexities and combinatorial explosion associated with existing parallel recognition processes in bioinformatics and in other technical fields, and that dramatically reduces associative memory search and retrieval effort. It would be further desirable to have systems and methods to perform DNA/RNA sequence matching with convenient database access, high-speed processing, improved resolution, accuracy, and cost efficiency.

BRIEF DESCRIPTION OF THE DRAWINGS

For a more complete understanding of the present disclosure, reference is now made to the following figures, wherein like reference numbers refer to similar items throughout the figures:

FIG. 6 illustrates a multi-resolution database and the segmentation of a target sequence into multiple sections, and the layer encoding applied to each of these sections for each track of the database, according to an exemplary embodiment of the present disclosure;

Figure 1:
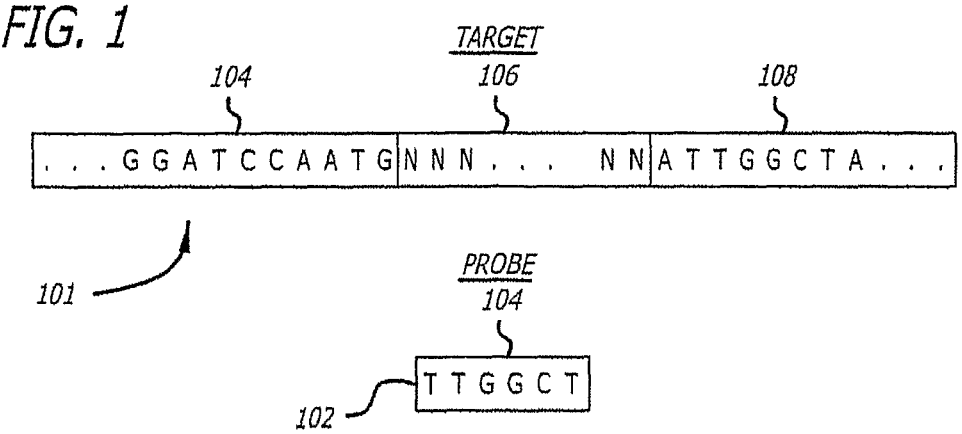
FIG. 1 illustrates an example of a genome target used as an input and a probe used as a query in a sequence searching method according to an exemplary embodiment of the present disclosure.

The exemplification set out herein illustrates particular embodiments, and such exemplification is not intended to be construed as limiting in any manner.

DETAILED DESCRIPTION

The following description and the drawings illustrate specific embodiments sufficiently to enable those skilled in the art to practice the systems and methods described herein. Other embodiments may incorporate structural, logical, process and other changes. Examples merely typify possible variations. Individual components and functions are optional unless explicitly required, and the sequence of operations may vary. Portions and features of some embodiments may be included in or substituted for those of others.

The elements that implement the various embodiments of the present system and method are described below, in some cases at an architectural level. Many elements may be configured using well-known structures. The functionality and processes herein are described in such a manner to enable one of ordinary skill in the art to implement the functionality and processes described herein.

The processing described below may be implemented in the form of special purpose hardware and/or in the form of software or firmware being run by a general-purpose or network or other specialized processor. Data handled in such processing or created as a result of such processing can be stored in any type of memory or other computer-readable medium as is conventional in the art. By way of example, such data may be stored in a temporary memory, such as in the random access memory of a given computer system or subsystem. In addition, or in the alternative, such data may be stored in longer-term storage devices, for example, magnetic disks, rewritable optical disks, and so on. For purposes of the disclosure herein, computer-readable media may comprise any form of data storage mechanism, including existing memory technologies as well as hardware or circuit representations of such structures and of such data.

It should also be understood that the techniques of the present system and method might be implemented using a variety of technologies. For example, the methods described herein may be implemented in software running on a programmable microprocessor, or implemented in hardware utilizing either a combination of microprocessors or other specially designed application specific integrated circuits, programmable logic devices, or various combinations thereof. In particular, the methods described herein may be implemented by a series of computer-executable instructions residing on a storage medium such as a carrier wave, disk drive, or other computer-readable medium. In addition to electronic and semiconductor hardware implementations, several important steps may be functionally implemented using non-electronic media and methodologies such as, for example, using optical components. Furthermore, analog media may provide a lower-cost alternative to digital media for storing or transmitting wavefunctions as described in the methods herein. As a result, it is feasible, in some embodiments, that the wavefunction may be processed starting from an analog storage medium, proceed via an analog processing chain, and then the pattern match results output as an analog signal without the need to pass through a step of conventional electronic digital representation, all according to the functional methods described herein.

One field of endeavor in which the present disclosure may be employed is in the field of genome sequence searching. However, as will be described below, the disclosure is not limited to genome sequence searching and may be employed in other fields involving the analysis of linear records, for example, where the analysis and interpretation of complex patterns are performed. Nonetheless, the following description will be limited to a genome sequencing search example for the sake of brevity. In addition, with respect to genome sequence searching, it should be noted that while the following description focuses primarily on DNA, the disclosure is not limited to use with DNA but can be utilized with data related to other genetic components such as, for example, RNA, tRNA, mRNA and rRNA.

The disclosure of a specific embodiment of a quantum computing associative memory system and method is now presented below. This disclosure illustrates several aspects that may be provided by this system and method, which may include one or more of the following features: encoding duality using an orthogonal basis; orthogonal transforms and domains; unitary operations; quantum field wavefunctions; superpositions of multiple quantum field wavefunctions and interference with superpositions of multiple quantum field wavefunctions.

As used herein, a "match" between a target and a probe may include a 100% match or a match with a lesser degree of similarity. As used herein, a "hit" means a match located from a search of a target using a probe.

The associative memory feature of the present disclosure is illustrated, for example, in the embodiment below in which location and retrieval from memory is determined by the content of the input instead of by some other proxy or label, such as an address, alphabetic index, hash table or any other external attribute, reference or pointer.

The first of several features to reduce hit detection and retrieval effort described herein is the use of superpositions of wavefunctions to process multiple layers of encoded data in parallel. A linear record, such as a genome DNA sequence, is mapped as a plurality of superpositions each comprising multiple layers. A location and retrieval task involves searching the entire database for matches between an input probe or query sequence and the target genome sequence. If a match is present, then its location is output. In the present disclosure this location corresponds, for example, to two coordinates: the index of the layer where the matching sequence is located; and the offset within the layer where the match is present. The wavefunction superposition comprising the database therefore may contain a two-dimensional search space in which any sequences in the database that match the probe may be located in this search space by a layer dimension index and an offset dimension index.

Another feature to help reduce hit detection and retrieval effort is the use of layer encoding modulation to create superpositions of wavefunctions such that the layer where a hit is located may be read by means of a layer profile.

In other words, one of the of the features of the present disclosure is the providing of an efficient method for first encoding, then later extracting, the layer index of any matches between the probe sequence and the target database. This implements an associative short-cut that avoids an exhaustive search of each layer in turn. Once the layer index has been identified, the full search space has been narrowed down to a single layer or page. This feature is described as measurement of the layer profile.

The layer profile allows all layers in a superposition to be processed as one layer, compressed into a single record, with the resulting output being a profile of the match correlation between probe and target and the match distance metric for each layer. This provides a faster and more efficient way to evaluate if any match is present between the probe (e.g., query or new experience) and the target (e.g., database or sum of past experiences), and if there is, to output the specific index of the layer in the superposition where that match is located.

As is described in greater detail below, the location of the match within the layer selected by the layer profile described above may be extracted by forming an interference viewpoint selected by the layer index. The interference viewpoint may be constructed by using one or more superpositions to interfere with the probe wavefunction. In the case where more two or more superpositions are used, as discussed further below, the process of constructing this viewpoint involves performing an extraction operation to combine the outputs of the first interference process. In this way, the first interference process may be used to generate intermediates (which may be temporarily stored in storage buffers during computations). These are common to both the layer profile process to read the layer index as mentioned above, and also the process to extract the interference viewpoint of that selected layer, which allows reading of a search coordinate equal to the offset position in that layer.

The layer profile process therefore comprises an interference between one or more superpositions and the probe wavefunction. The specific architecture associated with this process has the encoding of the layer index in each of the separate wavefunctions that are combined into superpositions.

Figure 5A:
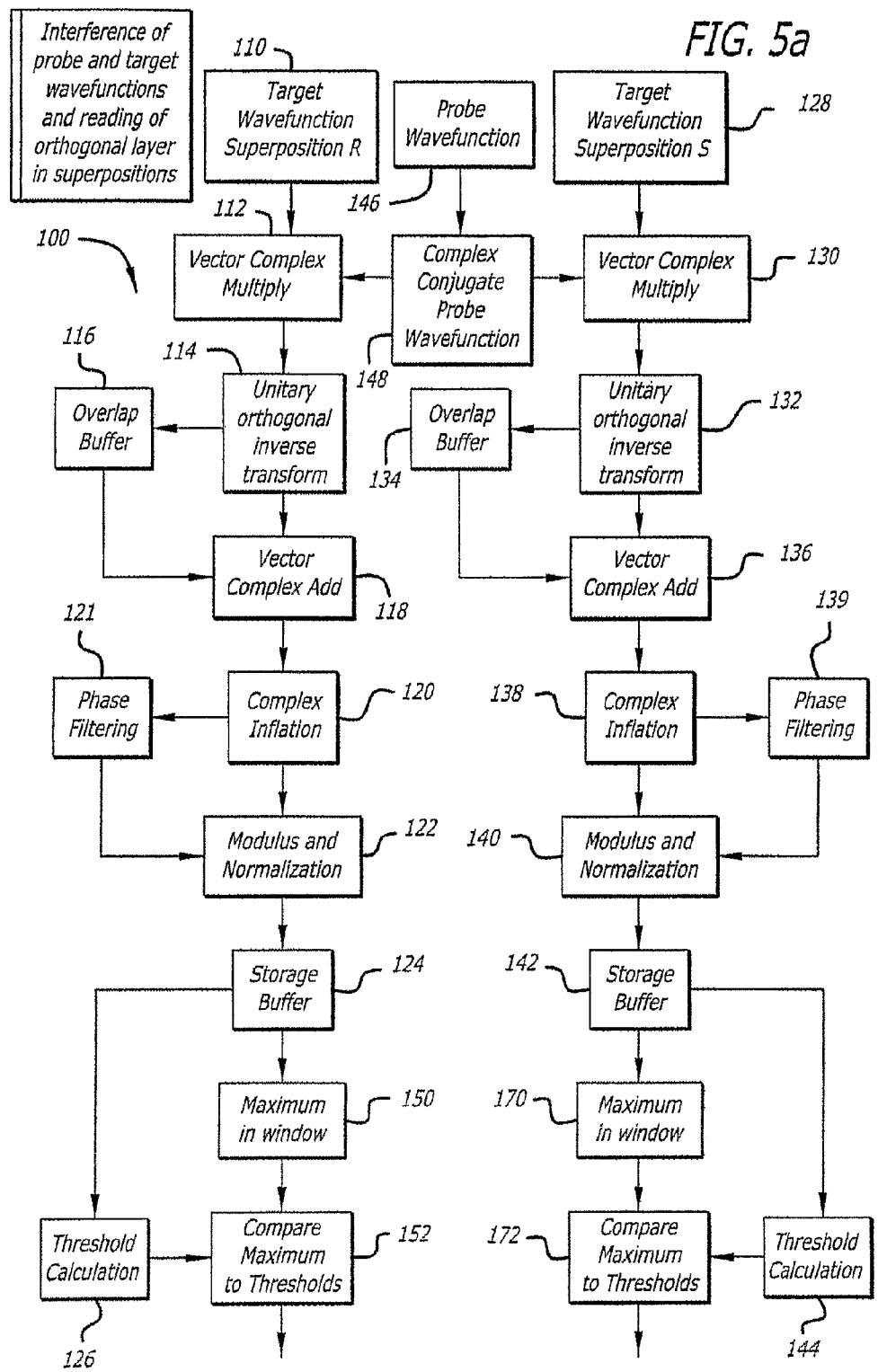
FIG. 5 illustrates a sequence searching method, using interference between the probe and target wavefunctions prepared by the methods of FIGS. 3 and 4 and the assessment of hits that are located, according to an exemplary embodiment of the present disclosure.
Figure 5B:
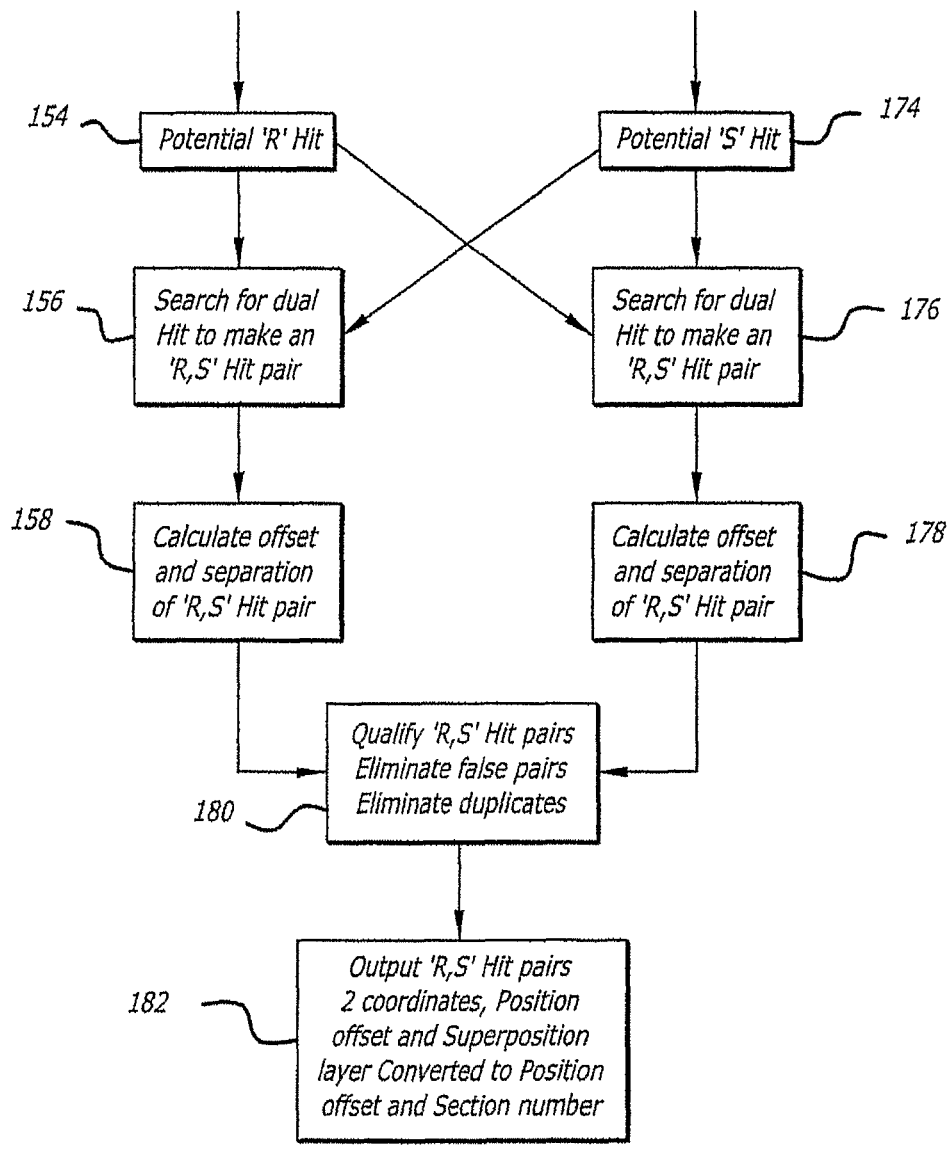

It should be noted that the layer profile may be used to process the entire target database for any and all matches to the input probe: it is a de novo calculation of the correlation between the probe and the target database for all reading frames and sequence alignments within the entire database sequence, such as the genome. The output of this distance calculation exists as the output of an interference process, and may be stored as an intermediate wavefunction. For example, as illustrated in FIG. 5 (to be discussed in more detail below), the output of the interference process is stored as intermediate wavefunctions in storage buffers 124 and 142. Here, two orthogonal superpositions (designated "R" and "S" and provided at steps 110 and 128 of FIG. 5) are used to generate the intermediate wavefunctions stored in storage buffers 124 and 142.

The specific properties of the layer encoding are such that layer encoding is designed to be orthogonal to position encoding. Because wavefunction superpositions are employed that actually comprise multiple wavefunction layers in a single wavefunction, each stage of the layer profile process is the size of a single dimension of the search space (i.e., a single wavefunction). It is the particular architecture of orthogonal encoding and decoding operations in the present disclosure that allows this processing gain to be realized. In practice this processing gain means that, using a data vector equivalent in size to a single dimension of the search space, it is possible to process a match correlation for an entire two-dimensional search space.

Additional aspects of the system and method of this disclosure will now be described in even greater detail for the particular embodiment of DNA sequence searching. An example of a genome used as an input in sequence searching is depicted in FIG. 1, wherein one or more genes are defined as sections 104, 106, and 108 of a nucleotide sequence on the DNA genome 101. The nucleotide bases are identified as A, T, C, or G. Bases designated as "N" are unknown and may be (e.g., in this case of DNA) A, T, C or G. An example of a probe 102 is also depicted in FIG. 1. Probe 102, in this example, has a base length of six bases. In general, a genome or sequence to be searched is referred to as a "target" below, and the target is typically separated into a number of sections of defined length for purposes of processing. Each section is further broken down into a number of frames as discussed below.

Figure 2:
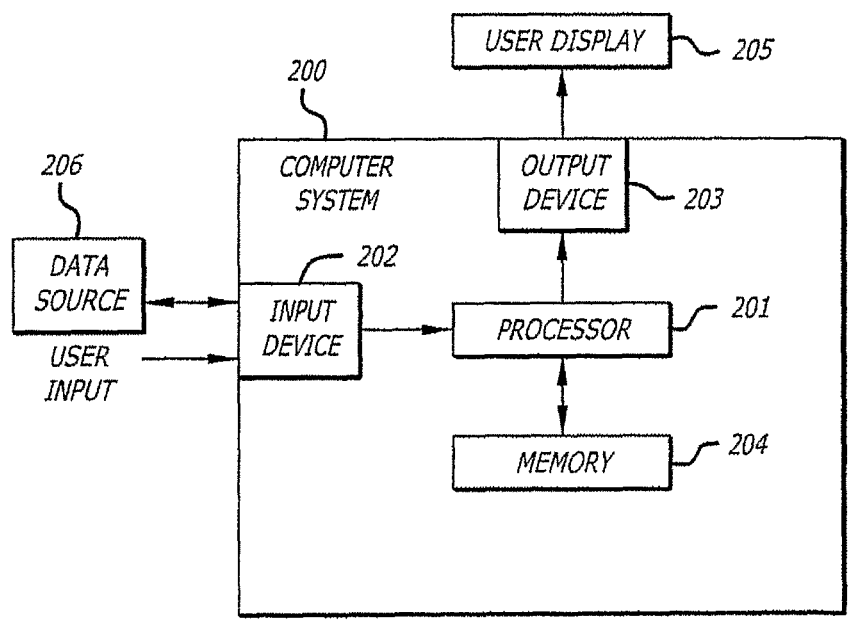
FIG. 2 illustrates a computer system that may be used to implement the search of the genome target of FIG. 1.

A block diagram depicting the components of a computer system that may be used with the methods of the present disclosure is provided in FIG. 2. Computer system 200 comprises an input device 202 for receiving data regarding a target to be searched and a probe (i.e., query) to use in conducting this search. The target may be, for example, linear data regarding genome 101 or other genetic sequences. The data may be received from data source 206, which may be, for example, another computing device coupled to computer system 200 using, for example, the Internet or a local area network. Input device 202 may include multiple ports for receiving data and user input. The user input may be dynamically interactive with computer system 200 and be responsive to information provided to the user on a user display 205 or other user output device. Typically, user input is received from conventional input/output devices such as, for example, a mouse, trackball, keyboard, light pen, etc., but may also be received from other means such as voice or gesture recognition.

An output device 203 is coupled with a processor 201 for providing output through various possible interfaces. Output to a user on user display 205 may be provided on a video display such as a computer screen, but may also be provided via printers or other means. Output may also be provided to other computer systems, devices or other programs for use therein. For example, computer system 200 may be a Web server used to provide data searching services as an application service provider. For example, search results may be presented on user display 205 as a map showing direct hits and close homologies for a given probe.

Input device 202 may be coupled with processor 201, which may be, for example, a general-purpose computer processor or a specialized processor designed specifically for use with the present disclosure. Processor 201 may also comprise, for example, multiple processors working in parallel. Processor 201 may be coupled with memory 204 to permit storage of data used in the methods described herein and to store computer programs to be executed by processor 201. Memory 204 may be implemented as several memories or may be partitioned for storage of different data types. Memory 204 may be used, for example, to provide numerous storage buffers for intermediates that are used in calculations for the searching methods described herein.

Figure 3:
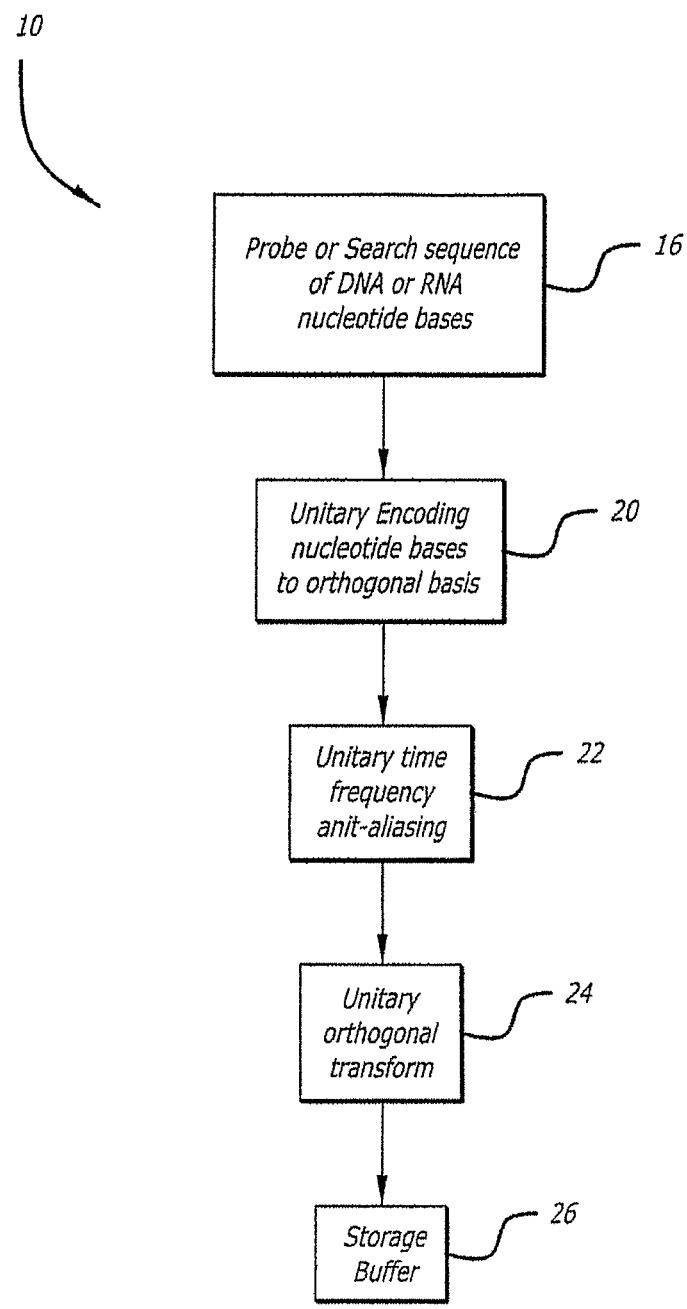
FIG. 3 illustrates the transformation of a probe sequence to a wavefunction for use in sequence searching according to an exemplary embodiment of the present disclosure.

FIG. 3 illustrates a method 10 for the transformation of a probe sequence (e.g., a DNA sequence) to a wavefunction for use in DNA or RNA sequence searching. The preparation of the DNA or RNA probe sequence by transformation to a wavefunction starts with an input probe or search sequence of DNA or RNA nucleotide bases 16. This is typically in the format of a text file, known as a "Fasta" file, where each nucleotide base of DNA or RNA is encoded using its initial letter. For example, each line of a Fasta file may contain up to fifty ASCII text characters encoding the same number of DNA or RNA nucleotide bases. For the purpose of the present description the probe or search sequence will be the instance of what is being searched for in a much larger database, such as a chromosome or genome, or any part or combination of these.

The probe sequence may encode any sequence of interest from the very short through to the very long. This may be, for example, a short oligonucleotide fragment such as a small interfering "siRNA" of just 22 bases, or a palindrome sequence, a duplex forming structure or any other possibility. The present method is may be used with short probe lengths such as, for example, one to twelve bases in length. Alternatively, very long DNA and RNA sequences of several thousands of base pairs may be used as the probe sequence.

The input sequence 16 is processed by a unitary encoding of the nucleotide base sequence to a vector in an orthogonal basis 20. As applied to DNA and RNA sequence searching, the present method achieves an orthogonal and unitary mapping between each of the four nucleotide bases (Adenine, Thymine, Guanine and Cytosine in the case of DNA; or Adenine, Uracil, Guanine and Cytosine in the case of RNA) and the four phase quadrants in a complex number plane (e.g., points around a unit circle). For example, this mapping in a graph in which the x-axis represents a real component and the y-axis an imaginary component may be represented as follows for a DNA sequence: A (1, 0), C (0, j), T (1, 0), and G (0, –j). The output of step 20 is a data representation of a vector of complex numbers. In this specific embodiment, the length of this complex vector is equal to the length in number of bases of the input probe nucleotide sequence (e.g., seven bases in length).

The output of step 20 is then passed to the next step in the process, which is a unitary time frequency anti-aliasing 22. This step is done to remove aliasing of position of the input sequence due to transform periodicity equal to the complex frame size (2N or 4,096 in the exemplary case discussed herein). Such aliasing may cause ambiguity in the orthogonal transform that would violate the unitary (or 1:1 mapping) principle of the present disclosure, which is desired for symmetry of information flow either backwards or forwards via a complex field equivalent. To preserve the unitary principle, this aliasing must be removed. This may be accomplished by appending to the output of step 20 an equal length complex vector comprising real and imaginary components each having all values of zero. The output of step 22 would therefore be a complex vector at least twice the length of the input probe nucleotide sequence. For this specific embodiment, an additional number of real and imaginary component with zero value are appended to the probe so that the output complex vector from step 22 has a length equal to twice the length of the frame size that will be used for encoding portions of the target sequence, which frame size is discussed further below. In the embodiment described below, the frame size is selected to be 2,048 bases, and so the output of step 22 is a complex vector with a length of 4,096 complex elements (where each complex element has a real and an imaginary component).

The output of step 22 is next processed by a unitary orthogonal transform 24. This maps the input data representation of a complex vector to an output complex vector in an orthogonal dimension or domain. In addition to the input and output domains being mutually orthogonal, each element of the input complex vector is equivalently represented by a basis function that is orthogonal to each of the other basis functions in that input domain. Symmetrically, each element of the output complex vector is equivalently represented by a basis function that is orthogonal to each of the other basis functions in that output domain.

While many possibilities exist for the unitary orthogonal transform 24 that meet the criteria specified above, for the purposes of the present embodiment the specific instance of the unitary orthogonal transform will be implemented as a discrete Fourier transform. Transforms that may be used in other embodiments include, for example, transforms based on prime number theory, Hadamard transforms, Sine, Cosine, Hartley, as well as many potential wavelet transforms.

Following the unitary orthogonal transform 24, the probe is now represented by a wavefunction in the form of a complex vector. For the specific example discussed below for a frame size of 2,048 bases, this complex vector contains 4,096 complex elements (where each complex element has a real and complex component). The probe is stored in storage buffer 26, to retain the probe in memory prior to interference with other wavefunctions from the target (discussed below). For purposes of later reference, this stored wavefunction is designated as φ. Storage buffer 26 may be implemented in memory 204 of computer system 200, or in another storage device. The stored probe wavefunction may serve as a resource that can be reused if multiple interference processes need to use this wavefunction. Such storage of the probe often may be more efficient and economical compared to serially repeating the wavefunction preparation process. This intermediate may also be used immediately without storage.

Figure 4:
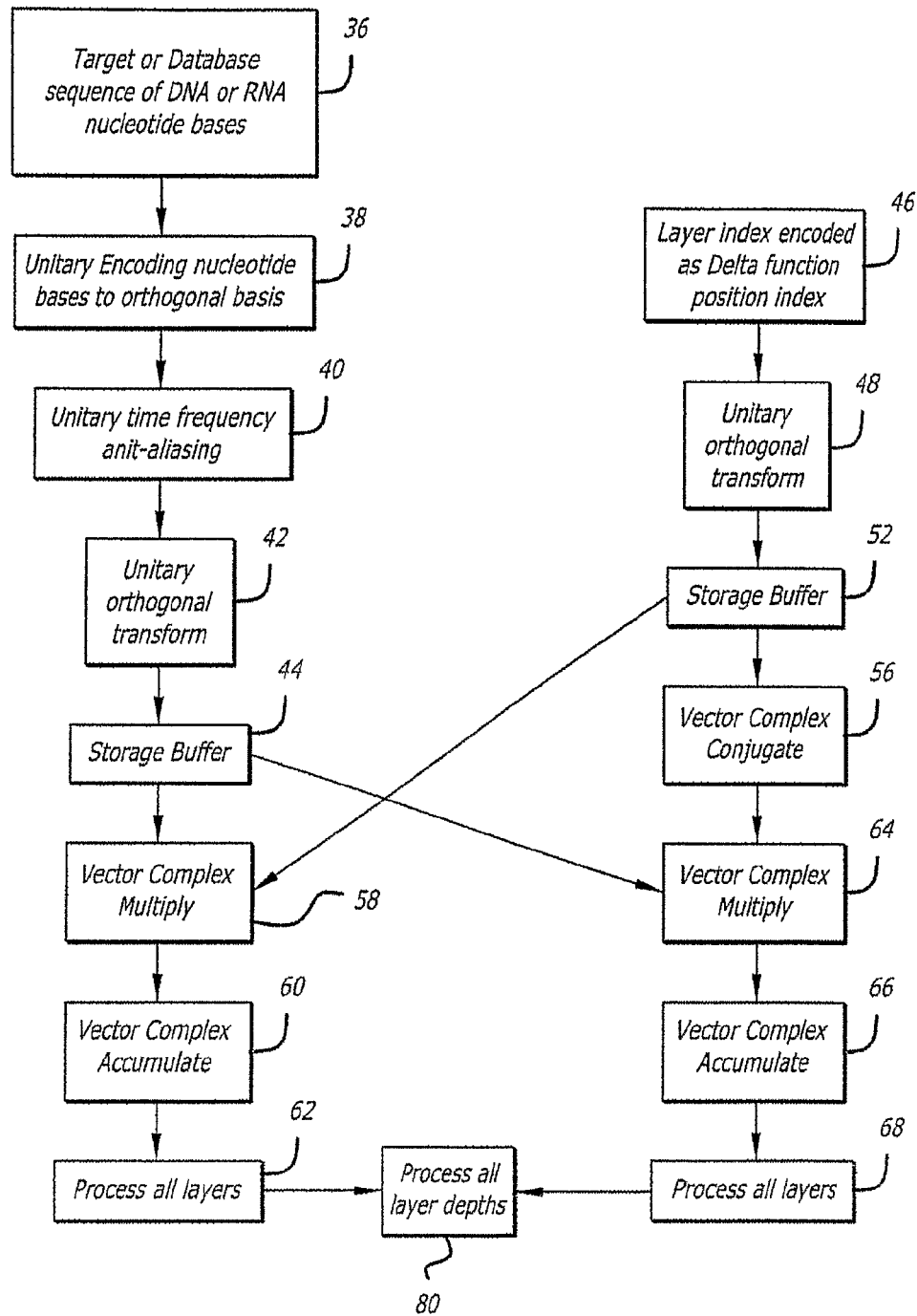
FIG. 4 illustrates the transformation of target sequence to superpositions of wavefunctions and layer encoding for use in sequence searching according to an exemplary embodiment of the present disclosure.

FIG. 4 illustrates the transformation of a target sequence (e.g., DNA genome 101) to superpositions of wavefunctions and layer encoding for use in searching the target sequence with a probe. More specifically, FIG. 4 schematically illustrates DNA/RNA target sequence preparation to a wavefunction form and the creation of orthogonal layer encoding superpositions.

Target sequence (sometimes referred to simply as a "target" herein) preparation begins with the input of a target sequence of DNA or RNA nucleotide bases 36. This is typically in the format of a text file, for example a "Fasta" file, where each nucleotide base of DNA or RNA is encoded using the initial letter of the base name.

The next four steps (namely, unitary encoding nucleotide bases to orthogonal basis 38; unitary time frequency anti-aliasing 40; unitary orthogonal transform 42; and storage buffer 44) are similar in functionality to the correspondingly-named steps in method 10 of the probe preparation process described above.

The input sequence 36 is processed by a unitary encoding of nucleotide base sequence to a vector in an orthogonal basis 38. As mentioned above, the input target sequence, which may be millions of bases in length, is typically broken down into smaller frames for processing using the present method. A frame size that is a power of two is typically selected for ease of use with the Fourier transform, but this is not a requirement of the method described herein. In the example discussed below, the target frame size (N) is selected to be 2,048 bases (N=2,048). Other sizes could also be used such as, for example, 4,096 or 8,192 bases. Hundreds and thousands or more of frames may be each processed as described below in order to encode the full length of a given target as superpositions of wavefunctions, for use in searching as described below.

Similarly as described above for probe preparation, this embodiment as applied to a DNA/RNA sequence search achieves an orthogonal and unitary mapping between each of the four nucleotide bases (Adenine, Thymine, Guanine and Cytosine in DNA; and Adenine, Uracil, Guanine and Cytosine in RNA) and the four phase quadrants in a complex number plane.

The output of step 38 is a data representation of a vector of complex numbers. In the embodiment described here, the length of this complex vector is equal to the length in bases of the given input frame from the target nucleotide sequence (e.g., N=2,048 bases). The output of step 38 is then passed to the next step in the process, which is a unitary time frequency anti-aliasing 40. Similarly as for the probe above, this step removes aliasing of position in one orthogonal domain with respect to the other orthogonal domain. Such aliasing may causes ambiguity in the orthogonal transform that violates the unitary (or 1:1 mapping) principle described above. In order to preserve the unitary principle this aliasing must therefore be removed. This may be accomplished by appending to the vector output of step 38 an equal length complex vector comprising zero real and imaginary components. The output of step 40 would therefore be a complex vector at least twice the length of the input target nucleotide sequence. In the example of N=2,048 bases, the output of step 40 is a complex vector having 2N or 4,096 complex elements (where each element has a real and an imaginary component).

The output of step 40 is next processed by unitary orthogonal transform 42. This maps the input data representation of a complex vector to an output complex vector in an orthogonal dimension or domain. In addition to the input and output domains being mutually orthogonal, each element of the input complex vector is equivalently represented by a basis function that is orthogonal to each of the other basis functions in that input domain. Symmetrically, each element of the output complex vector is equivalently represented by a basis function that is orthogonal to each of the other basis functions in that output domain.

While many possibilities exist for the unitary orthogonal transform 42 that meet the criteria specified above, for the purposes of the present embodiment the specific instance of the unitary orthogonal transform will be formalized as a discrete Fourier transform. As previously discussed, other transforms may also be used in other embodiments.

Following the unitary orthogonal transform 42, the target is represented by a wavefunction represented in the form of a complex vector (e.g., with 2N or 4,096 complex elements in this specific example), which may be stored in storage buffer 44. Storage buffer 44 stores this target wavefunction in memory for interference with other wavefunctions as part of encoding and preparing the target for later searching by the probe. Storage buffer may be implemented in memory 204 or in another storage device. The storage serves as a resource if multiple interference processes need to use this target wavefunction, and such storage may be more efficient compared to serially repeating the wavefunction generation process. For purposes of later reference, this intermediate wavefunction stored in storage buffer 44 is designated χ. This intermediate wavefunction may also be used immediately, for example in computations executed by processor 201, without storage.

As mentioned more generally above, the target is encoded as one or more superpositions of wavefunctions, and these wavefunctions are encoded with a layer index. The number of layers deep of wavefunctions used in a given superposition may vary, as will be discussed further below. As an example, the superpositions may be formed from 64 wavefunctions each corresponding to a frame from the target, and each of these wavefunctions may be encoded with a layer index, for example, ranging from 0 to 63 (corresponding to a superposition depth of 64 layers). The relationship between layer index and target frames is later discussed in greater detail.

According to the present disclosure, the specific properties of the layer encoding are such that layer encoding is designed to be orthogonal to position encoding. This property is illustrated in the disclosure beginning with steps 46 and 48. The layer index in this specific embodiment is encoded as a delta function position index 46. According to this approach, the position of the delta function along a linear position axis will map unitarily to the layer number that is to be encoded in each one of many potential layer instances. For example, for layer zero, the delta function will be at a position zero.

The delta function position index 46 is provided as an input to step 48, which is a unitary orthogonal transform 48. The delta function for each position corresponding to a layer is converted to a wavefunction using the unitary orthogonal transform. A discrete Fourier transform is used in the DNA sequence example here described, but other transforms may be used in other embodiments, as was mentioned above. The wavefunction in this example is a complex vector having 2N complex elements (e.g., 4,096 complex elements when using a frame size of 2,048 bases). This wavefunction may be stored in storage buffer 52, and for purposes of later reference is designated as θ. The vector complex conjugate of the wavefunction θ is calculated in step 56, and is designated as θ*.

Layer encoding may be accomplished by the combining of the two modulation wavefunctions θ and θ* with the target wavefunction χ. The encoding of the target with a wavefunction of a position index and a complex conjugate of that wavefunction assist with the later decoding of the position index when one or more matches are located in a search.

In the case, as here, where the unitary orthogonal transform 48 is the discrete Fourier transform, the two modulation wavefunctions may be represented as vectors equated to roots of unity: $\theta_k = e^{-j2\pi k\Delta/N}$ in the case of the vector in storage buffer 52, and $\theta^*_k = e^{j2\pi k\Delta/N}$ in the case of the output of the vector complex conjugate step 56.

Layer encoding of the target wavefunction χ may be accomplished by the following two operations: (i) a vector complex multiply step 58, which uses the complex vectors stored in storage buffer 44 and storage buffer 52 and performs a vector complex multiply between the two vectors; and (ii) vector complex multiply step 64, which uses the complex vectors stored in storage buffer 44 and the output vector of vector complex conjugate step 56 and performs a vector complex multiply between the two vectors.

The output from steps 58 and 64 will each be a complex vector of 2N complex elements in this embodiment (e.g., 4,096 elements for a frame length N of 2,048 bases). Each complex vector from steps 58 and 64 will correspond to a frame in the original target data, which has been layer encoded as two wavefunctions (from the use of an index and a conjugate of that index).

Each of the many vector outputs of vector complex multiply step 58 then pass to vector complex accumulate step 60. Step 60 calculates a superposition by accumulating several wavefunctions output from step 58. The number of wavefunctions accumulated will depend on the number (i.e., the layer depth) of wavefunctions that will be represented by each superposition output from step 60. In other words, the output of step 60 is a superposition calculated by additively combining multiple wavefunctions output from step 58, where each wavefunction has a different layer encoding, to create a superposition wavefunction ψR in step 62 after all layers have been accumulated. In equation form, $\psi R = \Sigma \chi^* \theta$ for all layers that are used to form the superposition (each layer corresponds to a different wavefunction χ that is output from storage buffer 44 and to an index wavefunction that is output from storage buffer 52).

In a corresponding manner, several output vectors from vector complex multiply step 64 pass to vector complex accumulate step 66, which additively combines multiple wavefunctions output from step 64, each with different layer encoding, to create a superposition wavefunction ψS in step 68 after all layers have been accumulated. In equation form, $\psi S = \Sigma \chi^* \theta^*$ for all layers that are used to form the superposition (each layer corresponds to a different wavefunction χ that is output from storage buffer 44 and to the conjugate of an index wavefunction that is output from step 56).

The encoding method described above is repeated as necessary to process all additional frames of input data from a target or database sequence. As additional frames are processed, additional superposition wavefunctions ψR 62 and ψS 68 will be output. It should be noted that as the target is encoded, that superposition wavefunctions are generally provided as superposition R, S pairs (ψR, ψS). Each superposition ψR, ψS in the example described here has 2N (e.g., 4,096) complex elements.

Steps 60 and 66 are performed to provide potentially very many superposition R, S pairs for a given superposition depth (e.g., a depth of 64 wavefunctions). In step 80, a database may be formed by repeating steps 60 and 66 for other superposition depths (e.g., for layer depths of 32, 16, 8, 4, 2, and 1 wavefunctions).

Also, as an option to the above approach, additional input data frames from the target or database sequence may be processed to extend the length of the output superpositions wavefunctions ψR 62 and ψS 68 instead of only varying the number of layers they contain. As a result, it is possible to create a wide range of output superposition wavefunctions ψR 62 and ψS 68 of various lengths and depths of encoded layers. This flexibility may be used to create multi-resolution wavefunction databases containing a plurality of tracks of varying lengths and depths of encoded layers. The advantage of such a multi-resolution format is that the search process has a range of different superposition depth options in the wavefunction database and may select the most efficient option as appropriate for any given search instance.

The many different possible ways of formatting and combining the output superpositions wavefunctions ψR 62 and ψS 68 so that they may be combined into an encoded target wavefunction database 80 for access during the actual searching process. One specific embodiment of database 80 is the multi-resolution database described below with respect to FIG. 6. The multi-resolution database may comprise numerous superposition R, S pairs (ψR, ψS) grouped into various tracks with each track having a different layer depth. In this embodiment, typically, the maximum useful layer depth has been found to be 128 layers, with 64 layers being more typical. However, other embodiments of the method disclosed herein may possibly use greater layer depths.

FIG. 5 illustrates a sequence searching method 100, using interference between the probe and target wavefunctions prepared by the methods of FIGS. 3 and 4 and including the assessment of hits that are located. More specifically, method 100 involves the search for and detection of any pattern matches in the target wavefunction superpositions and the reading of the position offset plus the layer index of any detected matches.

According to the present disclosure, the pattern matching search process performs an interference between the probe wavefunction and one or more superpositions of target wavefunctions that have been modulated according to their particular layer index, as was discussed above. In the diagram of method 100, two separate superposition wavefunctions are input: target wavefunction superposition R 110 and target wavefunction superposition S 128. Superpositions 110 and 128 may be a superposition R, S pair (ψR, ψS) to be processed next from among the many such R, S pairs that correspond to a given track (the preparation of which was discussed above).

Method 100 illustrates the parallel searching of many such corresponding superposition R, S pairs. The given track has been selected, for example, from the multi-resolution database for performing a search. Criteria that may be used for selecting the track to use are discussed later below.

The input probe wavefunction φ 146 is prepared by method 10 of FIG. 3. The complex conjugate of φ is calculated in step 148 and is designated φ*. The complex conjugate φ* is then interfered separately with each of ψR and ψS by performing a vector complex multiply operation in each of steps 112 and 130, respectively. The output from each step 112 and 120 is a complex vector having 2N or 4,096 complex elements in the specific example of an input frame length of N or 2,048 bases.

The outputs of vector complex multiply steps 112 and 130 are next each processed with a unitary orthogonal inverse transform in steps 114 and 132, respectively. These inverse transforms are the inverse of the transform that was previously used to prepare the probe and target wavefunctions above. While many possibilities exist for the unitary orthogonal inverse transforms 114 and 132 as mentioned earlier, for the purposes of the present embodiment the unitary orthogonal transform will be an inverse discrete Fourier transform.

As will be next discussed, overlapping portions selected from the incoming inverse transform vector outputs from steps 114 and 132 will be separately added to overlap buffer 116 and overlap buffer 134 respectively, to provide vector complex addition results at each of steps 118 and 136. These results are designated for later reference as $VCA_R$ and $VCA_S$, respectively. After the processing described below, each of the vector results $VCA_R$ and $VCA_S$ will be a complex vector of length N or 2,048 complex elements for the exemplary input target frame size of N or 2,048 bases. It should be noted that a benefit of the overlapping of successive frames is to create $VCA_R$ and $VCA_S$ data that is independent of the probe sequence occurrences in the target sequence, even when the probe sequence is contained in two separate but consecutive wavefunction frames input to steps 110 and 128.

More specifically, each of the complex vectors output from step 114 (each such complex vector is designated as "frame h" for purposes of discussion) is processed to overlap a portion of a given frame h with a portion of its predecessor frame using an overlap buffer 116 and a vector complex add operation at step 118. For discussion purposes, each predecessor and successor complex vector output from step 114 is designated as "frame h−1" and "frame h+1", respectively. For the example of an initial input target frame length of N or 2,048 bases, each frame h contains 2N or 4,096 elements. For purposes of discussion, the elements for frame h may be considered as divided into a first half of elements 0 to N−1, and a second half of elements N to 2N−1 (each half contains N elements). For each frame output from step 114, the vector elements 0 to N−1 from the first half of the frame are stored in an overlap buffer at step 116. Overlap buffers 116 and 134 may be any suitable form of memory or other storage.

Next, in step 118 each of vector elements N to 2N−1 in the second half of a new frame h output from step 114 is added using vector complex add step 118 to the corresponding elements 0 to N−1 in the first half of the preceding output frame h−1, which was previously stored in overlap buffer 116. In other words, element 0 is added to element N, element 1 is added to element N+1, and so forth, and element N−1 is added to element 2N−1. The output from step 118 ($VCA_R$) is a set of N complex correlations 0 to N−1 for each incoming frame h. The total number of vectors $VCA_R$ output from step 118 is one for each frame input in steps 110 and 128. During loop processing, the total number of vectors $VCA_R$ output from step 118 is equal to the number of wavefunction superposition frames input in steps 110 and 128.

The first half (elements 0 to N−1) of the same new output frame h from the inverse transform 114 is stored in overlap buffer 116 until it is brought together with the second half (elements N to 2N−1) of the next output frame h+1 from inverse transform 114. As a result of this repeated overlap and vector addition processing, vector complex add 118 outputs a vector $VCA_R$ with a length that is half that of the output vectors from inverse transform 114.

In a similar manner to that described immediately above, each of many complex vector outputs from inverse transform step 132 is processed to overlap each frame with its predecessor and successor frames using overlap buffer 134 and vector complex add 136. As a result of this repeated overlap and vector addition process, vector complex add 136 outputs a vector $VCA_S$ with a length that is half that of the output vectors from inverse transform 132. The output from step 136 ($VCA_S$) is a set of N complex correlations 0 to N−1 for each incoming frame h.

The next steps involve processing the output vector $VCA_R$ of vector complex add step 118 via a complex inflation step 120, and processing the output vector $VCA_S$ of vector complex add step 136 via a complex inflation step 138. For each complex inflation step 120 and 138, each element of the vector $VCA_R$ and $VCA_S$, respectively, is raised to the third power using vector complex multiplication. In other embodiments, it should be noted that other powers or other manners of inflation may used. Complex inflation may assist in separating background noise in vectors $VCA_R$ and $VCA_S$ from peak signals therein that correspond to potential matches between the probe and the target database.

The outputs from complex inflation steps 120 and 138 may be processed using optional phase filtering steps 121 and 139. Typically, this is designed to select direct correlates and exclude phase rotated correlates since these are of greater interest in representing a pattern match. The outputs from this phase filtering are provided to modulus and normalization steps 122 and 140, respectively. Each of these steps 121 and 139 involves phase scaling by multiplying each complex element of each of the inflated vectors by a phase scale factor. The phase scale factor may be determined by the phase of the complex element. For example, the phase scale factor F may be cosine (arctangent (imaginary/real)) for the interval where real is positive. In the case where the real is less than or equal to zero, the phase scale factor F is zero. The phase filtered complex value output is (F*real, F*imag). The phase scaling may eliminate correlations that are out of phase. For example, there may be a match that is not a direct phase match to a probe, but instead is a rotation of that phase (e.g., the same sequence rotated by 90°).

The two parallel processing paths continue with the providing of the output of complex inflation step 120 to modulus and normalization step 122, and providing of the output of complex inflation step 138 to modulus and normalization step 140. Each of the modulus and normalization steps 122 and 140 involves calculation of the real modulus of each input complex element followed by a multiplication by a normalization scale factor that is constant for all elements in the input vector to step 122 or 140. The normalization scale factor may be determined using the theoretical maximum correlation value corresponding to the vector outputs from steps 114 and 132. The normalization scale factor may be calculated as the desired output peak height divided by a total input energy calculated according to the energy in the encoding of a single base, squared to reflect 100% correlation, times the number of bases raised to the third power to account for inflation, times the gain of the unitary orthogonal transform, times the gain of the unitary orthogonal inverse transform. In the case where each base is encoded by a complex value of magnitude 1,000, and using discrete Fourier transforms of 4,096 complex values, for a normalized peak of 687 the scale factor is $1e^{26}$. One aspect of the foregoing is that the normalization scale factor may be proportional to the reciprocal of the cube of the count of effective bases in the probe.

The output of each step 122 and 140 is a vector of scalar numbers (each vector is designated as $RV_R$ and $RV_S$, respectively) representing the scaled magnitude of the corresponding input complex vector elements. For example, for an exemplary input frame length of N or 2,048 bases, $RV_R$ and $RV_S$ contain N or 2,048 real numbers. Each of the vectors $RV_R$ and $RV_S$ is a correlation at a particular base position between the probe sequence and the target sequence. It should be noted that this correlation may be measured at every base position in the target sequence.

The outputs of steps 122 and 140 may be temporarily saved to storage buffers 124 and 142, respectively. These storage buffers may be used to hold these normalized results of the superposition R and S wavefunction interferences with the probe wavefunction so that the results may be further analyzed to determine if any hits or significant similarities are present. In this specific context, a "hit" refers to a peak value in the normalized data output from step 122 or 140.

In typical use, there is a stream of real vectors $RV_R$ and $RV_S$, with corresponding $RV_R$ and $RV_S$ vectors stored in storage buffer 124 or 142 for each superposition wavefunction R, S pair ($\psi R$, $\psi S$) that entered method 100 at steps 110 and 128. The number of $RV_R$, $RV_S$ vector pairs will depend, for example, on the resolution track from the multi-resolution database that was selected for searching. The real vectors typically abut one another directly (i.e., this process is like the assembly of one long real vector, with a length depending, for example, the number of layers being processed in parallel). The $RV_R$ and $RV_S$ vectors are examined for peaks that correspond to high correlations between the probe and the target.

Hit Detection Process

In an attempt to capture all potentially significant matches between the probe and target sequences, the hit detection process described below contains several steps. These steps are designed to identify all potential candidates, then to perform a more rigorous qualification of these candidates to attempt to eliminate false detection events. The hit detection process outputs qualified events comprising a pair of hits, one each from the parallel R and S wavefunction interference processing paths described above. However, as part of the hit detection process, the real vectors $RV_R$ and $RV_S$ are initially each screened for hits independently. This approach improves the likelihood that all significant matches between the probe and target sequences will be found since two detection opportunities are thus created for each potential match.

The hit detection process begins with a threshold calculation at step 126, which is applied to data from real vector $RV_R$ obtained from storage buffer 124 and a threshold calculation at step 144, which is applied to data from real vector $RV_S$ obtained from storage buffer 142. In each case, the normalized magnitude data are analyzed using statistical methods to calculate the mean and standard deviation of each set of data. In threshold calculation 126 two threshold values are calculated for the R wavefunction interference data, and in threshold calculation 144 two thresholds are calculated for the S wavefunction interference data.

Each pair of thresholds consists of a primary threshold and a secondary threshold, with the primary threshold being greater than the corresponding secondary threshold. These thresholds are calculated by adding the mean value to a multiple of the standard deviation value of the respective data set. For example, the multiples may be sixteen times in the case of the primary threshold and six times in the case of the secondary threshold. For the primary threshold a larger multiple is applied to the standard deviation value, and for the secondary threshold a smaller multiple is applied to the standard deviation value. In addition, a tertiary threshold is calculated for each data set using the combined means from steps 126 and 144 plus a multiple of the combined standard deviations from steps 126 and 144. This multiple is, for example, sixteen times the combined standard deviations. The tertiary threshold is used to test the combined maximum values in a pair of R, S hits. The use of the primary, secondary and tertiary thresholds is described below.

The next steps in the detection process are the determination of a maximum in a window in a step 150, which is applied to the data from the R wavefunction interference in storage buffer 124, and a maximum in a window in a step 170, which is applied to the data from the S wavefunction interference in storage buffer 142. The window length is in each case equal to the effective length of the probe sequence, where the effective length refers to the number of coding bases in the probe sequence, (but not counting gaps or bases with a zero input weighting—for example, a value $\gamma_k$ of zero as discussed below). Using a window size determined in this manner attempts to account for a hypothetical worst case scenario in which the probe sequence repeats itself as two adjacent sequences in the overall target sequence.

The window is advanced across the full length of each real vector $RV_R$ and $RV_S$. The window is advanced, after each selection of a maximum value, by a number of index positions in vector $RV_R$ or $RV_S$ equal to the total window length so that no given sequence position of the real vector is examined in step 150 more than once. A maximum value is selected from within the window for each vector $RV_R$ or $RV_S$ at each position in its advance along the corresponding vector.

The output of maximum in window step 150 is the index position (selected from positions 0 to N−1 in this example) and magnitude of the maximum value within the real vector $RV_R$ from storage buffer 124. A value and index data pair is output for each advance of the window along $RV_R$. Similarly, the output of maximum in window step 170 is the index position and magnitude of the maximum value within the real vector $RV_S$ from storage buffer 142. A value and index data pair is output for each advance of the window along $RV_S$.

The compare maximum to thresholds step 152 first tests whether the maximum value output from maximum in window step 150 meets or exceeds the primary threshold value derived in threshold calculation step 126. If it does, the result is considered to be a "Potential R Hit" 154 that is processed further as described below. Each Potential R Hit corresponds to a position and magnitude in $RV_R$.

Similarly, compare maximum to thresholds step 172 first tests whether the maximum value output from maximum in window step 170 meets or exceeds the primary threshold value derived in threshold calculation 144. If it does, the result is a "Potential S Hit" 174 that is processed further as described below. Each Potential S Hit corresponds to a position and magnitude in $RV_S$.

Alternatively, if the maximum value output from maximum in window step 150 is below the primary threshold value derived in threshold calculation step 126, and the maximum value output from maximum in window step 170 is below the primary threshold value derived in threshold calculation step 144, processing will continue by returning to maximum in window step 150 and maximum in window step 170, advancing the windows along each vector $RV_R$ or $RV_S$ to generate new maxima for testing in the compare maximum to thresholds step 152 and compare maximum to thresholds step 172 as described above.

If a Potential R Hit 154 exists, a search is performed in step 176 for the existence of a corresponding or dual hit in an attempt to make an "R, S Hit Pair". It should be noted that if a real correlation between the probe and target exists, then two significant corresponding correlations that were calculated from the superposition R and S wavefunctions (as was discussed earlier above) should also exist. An R, S Hit Pair would correspond to these two correlations and consist of an R hit and an S hit. The method described below intelligently searches for a corresponding or dual R hit or S hit in a range in which such a hit is expected to be if it corresponds to a truly significant correlation between the probe and the target. In general, the positional separation will be two times the layer number that the signal causing the correlation peaks to appear was earlier encoded into. For example, as will become more clear from the discussion below, if the hit is in a portion of the target sequence that was encoded into layer 3, the positions of the R hit and S hit will be separated by six positions in the position index used for the elements of real vectors $RV_R$ or $RV_S$.

Step 176 first tests, based upon the position of the Potential R Hit within the window used in step 150, if the entire range of possible dual S hit positions (i.e., corresponding to the Potential R Hit) was already included within the window used for the obtaining the S maximum from vector $RV_S$ in step 170. The entire range of possible dual S hit positions is defined relative to the Potential R Hit position by the largest separation delta generated by layer encoding. For any target track 902 (discussed further below) being processed, it is known how many layers have been combined (i.e., the depth of the superposition wavefunctions used). According to the exemplary multi-resolution database 900 (illustrated in FIG. 6), the largest separation delta generated by layer encoding is equal to twice the number of layers in that superposition.

If the entire range of possible dual S hit positions was included in the window of step 170, then the S maximum from step 170 may be used as the possible dual S hit corresponding to the Potential R Hit 154. Alternatively, if the entire range of possible dual S hit positions was not included in the window of step 170, then a search of the vector $RV_S$ is done to select the maximum value from within the entire range of potential dual S hit positions in $RV_S$ for use as the S maximum.

Next, the separation delta of the R and S maxima is calculated. The "separation delta" is equal to the position of the R maximum minus the position of the S maximum. The separation delta is then tested to see if it meets the following three conditions: (i) the separation delta is non-negative, (ii) the separation delta is even-numbered, and (iii) the separation delta is within the range of position separation generated by layer encoding, which as mentioned above, is equal to twice the number of layers in that superposition.

If the separation delta satisfies all of the above three conditions, the magnitude of the S maximum is compared against the secondary threshold previously calculated in threshold calculation step 144. If the magnitude of the S maximum meets or exceeds the secondary threshold, then the sum of the magnitudes of the R and S maxima is compared against the tertiary threshold previously calculated from steps 126 and 144. If the sum of the magnitudes of the R and S maxima is greater than or equal to the tertiary threshold, then the R and S maxima are passed as a potential dual R hit and S hit pair (or simply "R, S hit pair") to step 178.

Step 178 calculates the offset and separation of the potential dual R, S hit pair. Specifically, step 178 finds the position midpoint between the R and S maxima and records this as the offset of the R, S hit pair. In equation form: position midpoint=(position$_R$ maximum+position$_S$ maximum)/2. The separation delta of the two maxima is also determined. The separation delta is equal to the position of the R maximum minus the position of the S maximum.

Similarly as was described above for the existence of a Potential R Hit, if a Potential S Hit 174 exists, a search is performed in step 156 for the existence of a dual hit in an attempt to make an R, S Hit Pair. Step 156 first tests, based upon the position of the Potential S Hit within the window used in step 170, if the entire range of possible dual R hit positions (i.e., corresponding to the Potential S Hit) was already included within the window used for the obtaining the R maximum from vector $RV_R$ in step 150. The entire range of possible dual R hit positions is defined relative to the Potential S Hit position by the largest separation delta generated by layer encoding.

If the entire range of possible dual R hit positions was included in the window of step 150, then the R maximum from step 150 may be used as the possible dual R hit corresponding to the Potential S Hit 174. Alternatively, if the entire range of possible dual R hit positions was not included in the window of step 150, then a search of the vector $RV_R$ is done to select the maximum value from within the entire range of potential dual R hit positions in $RV_R$ for use as the R maximum.

Next, following step 156, is step 158, in which the separation delta of the R and S maxima is calculated. The "separation delta" is equal to the position of the R maximum minus the position of the S maximum. The separation delta is then tested to see if it meets the following three conditions: (i) the separation delta is non-negative, (ii) the separation delta is even-numbered, and (iii) the separation delta is within the range of position separation generated by layer encoding.

If the separation delta satisfies all of the above three conditions, the magnitude of the R maximum is compared against the secondary threshold previously calculated in threshold calculation step 126. If the magnitude of the R maximum meets or exceeds the secondary threshold, then the sum of the magnitudes of the R and S maxima is compared against the tertiary threshold previously calculated from steps 126 and 144. If the sum of the magnitudes of the R and S maxima is greater than or equal to the tertiary threshold, then the R and S maxima are passed as a potential dual R,S hit pair to step 178.

Step 158 calculates the offset and separation of the potential dual R,S hit pair. Specifically, step 158 finds the position midpoint between the R and S maxima and records this as the offset of the R,S hit pair. In equation form: position midpoint=(position$_{R\ maximum}$+position$_{S\ maximum}$)/2. The separation delta of the two maxima is also determined. The separation delta is equal to the position of the R maximum minus the position of the S maximum.

As mentioned above, the processing steps 150, 152, 154, 156 and 158 provide a substantially parallel path to the processing steps 170, 172, 174, 176 and 178, assisting in ensuring that the R and S normalized interference data are initially each screened for hits independently. This approach attempts to ensure that all significant matches between the probe and target sequences will be found since two detection opportunities are created for each match between the probe and the target. The results from these two parallel paths converge in step 180, which qualifies the R,S Hit Pairs. More specifically, step 180 eliminates R,S Hit Pair duplicates from these results (e.g., a duplicate R,S Hit Pair may have arisen as a result of using the parallel detection processes discussed earlier).

As will be discussed in more detail below, when originally preparing the target for searching, the target may be divided into a number of sections (e.g., 128 sections, designated as $S_0 \ldots S_{127}$) with each section encoded to one of the layer indices used for forming the layer-encoded superposition wavefunctions. In step 182, data for each of the R,S Hit Pairs detected in the preceding steps is used to generate the following data for each R,S Hit Pair: (i) a position offset, and (ii) a target section number. The target section number may be used with the position offset to identify the location in the target sequence that matches the probe sequence for the given R,S Hit Pair. The position offset is calculated from the offset of the R,S Hit Pair, which is equal to the position midpoint between the R and S maxima plus an offset of the frame size N for each frame of the target input in steps 110 and 128.

The superposition layer index is obtained by halving the layer separation delta from steps 158 and 178 (equal to the position of the R maximum minus the position of the S maximum). In the exemplary multi-resolution database 900 shown in FIG. 6, the number of sections in each layer varies from two for track 0 (64 deep) to sixty-four for track 5 (2 deep). Accordingly, the superposition layer index is multiplied by the number of sections per layer in the track 902 being processed to obtain the target section number. For example, in the case of a layer separation delta for a R,S dual hit of 16, the superposition layer index of this hit pair would be 8. If track 0 (64 deep) of database 900 in FIG. 6 were being processed, the target section number would be obtained by multiplying 8 by 2, where two is the number of sections in one layer.

The separation delta of the two maxima (as mentioned above, the separation delta is equal to the position of the R maximum minus the position of the S maximum), is divided by two to give the superposition layer number in which the hit was detected. The superposition layer number is then multiplied by the number of target sections originally included in each layer in order to yield the target section number (e.g., a number selected from the range 0 to 127 in the specific example discussed herein) in which the matching sequence is located.

Multi-Resolution Database

FIG. 6 illustrates a multi-resolution database 900 and the segmentation of a target sequence into multiple sections (designated as $S_0 \ldots S_{127}$), as was mentioned above. Multi-resolution database 900 may be optionally used with the searching method discussed above. However, in other embodiments, different forms of data structure or databases may be used to store the encoded probe and/or target used with the searching methods earlier discussed. For purposes of illustration, genome 101 is shown here as divided into 128 sections. In other embodiments, other numbers of sections may be used.

As discussed above, the multi-resolution database 900 may be organized in a number of different tracks 902 of varying resolutions. Each track 902 corresponds to a different superposition layer depth. For example, Track 1 corresponds to a preparation of all sections using superpositions that are 32 layers of data deep (as was discussed above).

A layer encoding index 904 may be applied to each of these sections for each track 902 of the database as illustrated. For example, the superpositions created for data in sections $S_0$ and $S_1$ of Track 0 are encoded with layer index 0, and sections $S_2$ and $S_3$ are encoded with layer index 1. For Track 6, since it is only one layer deep, it should be noted that only one set of superpositions R is needed, since the superpositions S will be identical for one-layer depth.

Figure 7:
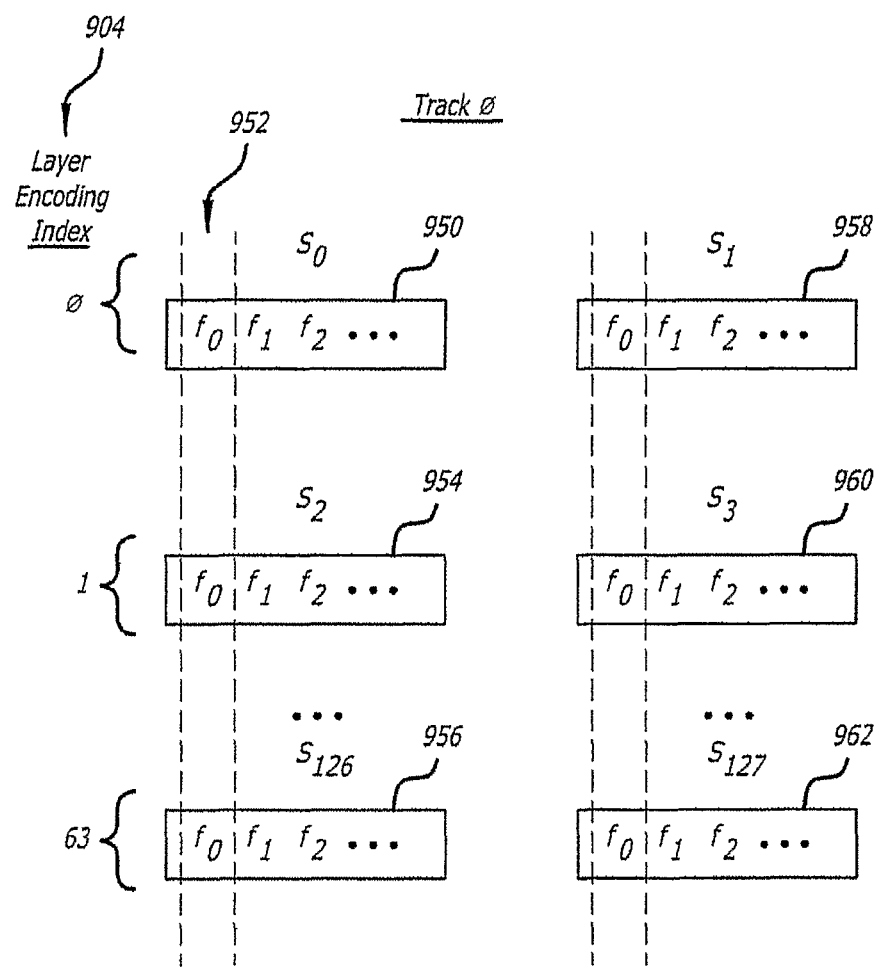
FIG. 7 illustrates the further segmentation into individual frames of the sections of an exemplary track zero of the multi-resolution database of FIG. 6 according to an exemplary embodiment of the present disclosure.

FIG. 7 illustrates the exemplary further segmentation into individual frames (e.g., $f_0, f_1, f_2, \ldots$) of the sections of Track 0 of multi-resolution database 900. Each section S from database 900 may be organized as a number of frames. The number of frames in each section may be determined, for example, by dividing the total base length of the target by the number of sections (e.g., 128) multiplied by the frame base length (e.g., 2,048 bases).

For example, for a target length of 25,165,824 bases, a total section number selected to be 128 sections, and a frame length selected to be 2,048 bases, the number of frames per section is 96. Thus, frame group 950 corresponding to section $S_0$ will have 96 frames, and frame group 958 corresponding to section $S_1$ will have 96 frames.

In one approach, a superposition wavefunction R, S pair ($\psi R, \psi S$) is calculated using a frame selected from the same relative position for each layer encoding index 904. For example, $\psi R$ and $\psi S$ are calculated using a superposition of 64 wavefunctions, with each wavefunction corresponding to frame $f_0$ selected from the frame group 950, 954, . . . , 956 as indicated by the dashed lines at 952. A ($\psi R, \psi S$) pair is next calculated for each frame $f_1$, and so on for each corresponding frame position for Sections $S_0, S_2, \ldots, S_{126}$. The same approach is also applied to frame groups 958, 960, . . . , 962 for Sections $S_1, S_3, \ldots, S_{127}$.

To maintain database continuity, it is typically necessary and desirable to remove boundary effects or discontinuities, which may occur as explained below. To accommodate this, there will be an additional overlap frame that is present in each track of more than one-layer deep. The result of the calculations in the simple exemplary case illustrated above will be a total of 1+96+96=193 ($\psi R, \psi S$) pairs for Track 0. These calculations may then be done for each track 902 so that database 900 in general contains a set of ($\psi R, \psi S$) pairs for each track 902, which can be selected and used for searching with a probe as earlier discussed.

As referred to above, overlapping of successive frames creates $VCA_R$ and $VCA_S$ data that is independent of the probe sequence occurrences in the target sequence, even when the probe sequence is contained in two separate, but consecutive wavefunction frames input to steps 110 and 128. The special case where the probe sequence crosses a section boundary is generally dealt with in database 900 by making each track comprise successively ordered sections: the last frame of section 0 is followed by the first frame of section 1, and within all tracks 902 shown in the exemplary case section 0 is followed by section 1.

There is, however, a separate worst case where the probe sequence may cross a section boundary that lies at the end of a track layer. An example of such a case would be a probe that had its first half as the last three bases in section 63 and its second half as the first three bases of section 64. This worst case can be made equivalent to a more normal case by a formatting of database 900 so that duplicates of the last frame of the endmost sections of each track are encoded as an extra frame at the beginning of the next layer of the superposition. For the first section 0, the place of this overlap is filled by a frame of zero data for the purposes of the frame-aligned summation that creates the superposition of layers. Therefore, in database 900 in the exemplary case, the successive layers are arranged so that the section at the end of the track in one layer is followed in the original input information sequence by the first section of the next layer in the superposition. This allows the section boundary to be made transparent as far as output position index such that the same sequence position is represented by the following information: (start of next layer−x) and (end of previous layer+N−x), where x is less than N and the start and end positions are the chromosomal target position indices of the first base in each of the corresponding frames.

In the worst case example where a probe sequence is present in the target with its first half as the last three bases in section 63 and its second half as the first three bases of section 64, there would be a hit detection at a position equal to the starting position of section 64 minus 3 bases. This hit would be generated by $VCA_R$ and $VCA_S$ data that combines the overlap frame from the end of section 63 as a first frame, with the first frame of section 64 as a second frame. As indicated previously, vector elements N to 2N−1 in the second half of a second frame output from step 114 are added using vector complex add step 118 to the corresponding elements 0 to N−1 in the first half of the first output frame, which was previously stored in overlap buffer 116.

In one example of the above, the database is created to maintain continuity across more than 10,000 frames of the frames in the target sequence.

Searching Process and Interaction with
Multi-Resolution Database

Figure 8:
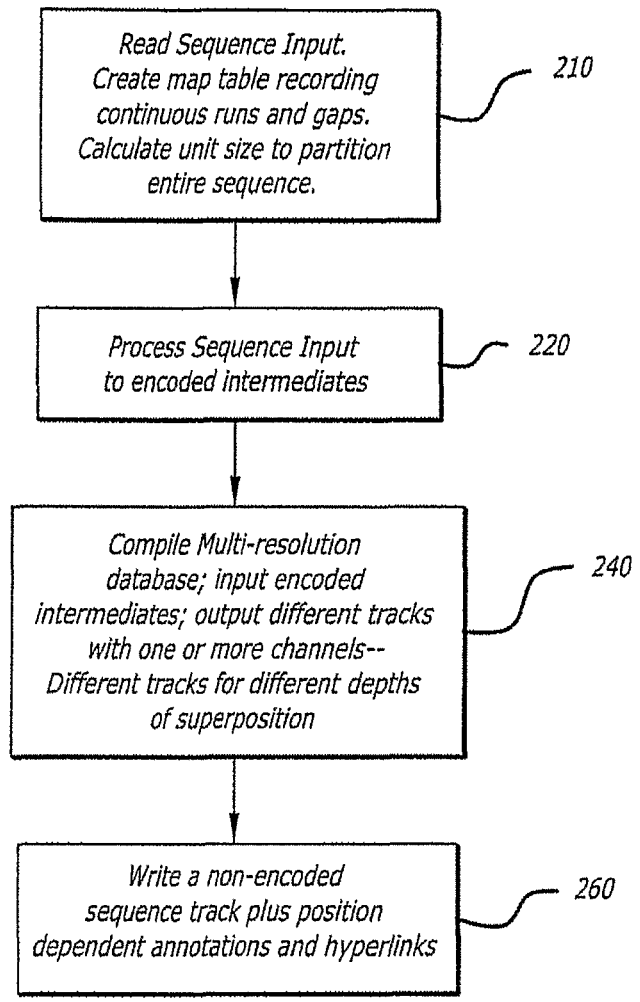
FIG. 8 illustrates the preparation of target data, the multi-resolution database of FIG. 6, and a non-encoded sequence track, according to an exemplary embodiment of the present disclosure.

FIG. 8 illustrates the preparation of target data and certain interactions that may occur with multi-resolution database 900. A target sequence is read in step 210. A map table may be created that records continuous runs of zeroes and gaps in the target sequence. The runs of zeroes and gaps may be identified for the purpose of removing them from the data prior to preparing database 900. The locations may be later used when interpreting the search results and determining match positions in the target sequence. A unit size is calculated to partition the entire target sequence (for example, the number of frames per section discussed above) for forming database 900.

In step 220, the target may be encoded to intermediates as illustrated in FIG. 4. In step 240, the intermediates may be encoded to form multi-resolution database 900. Different tracks may be output from database 900 with one or more channels. An R superposition plus an S superposition is an example of two channels of wavefunction frame data, and the final track 6 of database 900 is an example with one channel of wavefunction frame data. The different tracks correspond to different depths of superposition as discussed above.

It is typically desired to want to exploit the maximum number of layers of superposition can be searched in parallel in any one particular instance in order to have the maximum search efficiency. The layer depth of superpositions that can be processed typically depends on the number of defined bases in the probe sequence. The longer the probe, the greater layer depth of superpositions that can be used in doing the search because of the greater uniqueness of the probe.

For purposes of explanation, the layer depth limit is related to the signal-to-noise ratio (SNR). A longer probe will have a higher SNR than a shorter probe. For each length of probe, there is typically a superposition layer depth that can be effectively processed. It is desired to have a database that has different layered depths in it that may be selected as optimal for different probes. For example, the database will have greater layer depths for longer probes, shorter layer depths for shorter probes, and for the shortest probe, it may have a depth of only a single layer.

In step 260, a non-encoded target sequence track may be created. This track is separate from, but may be synchronized on a frame basis, with the wavefunction frames in other tracks. As a result, this non-encoded target sequence track may be more efficiently accessed for any wavefunction frame by using the corresponding frame counter or index. This non-encoded track may include position dependent annotations at various positions along the target sequence and/or hyperlinks that may present additional information to a user or permit a user to interactively link to additional information about various positions on the target while interacting with and interpreting search results (e.g., while viewing results on user display 205).

Figure 9:
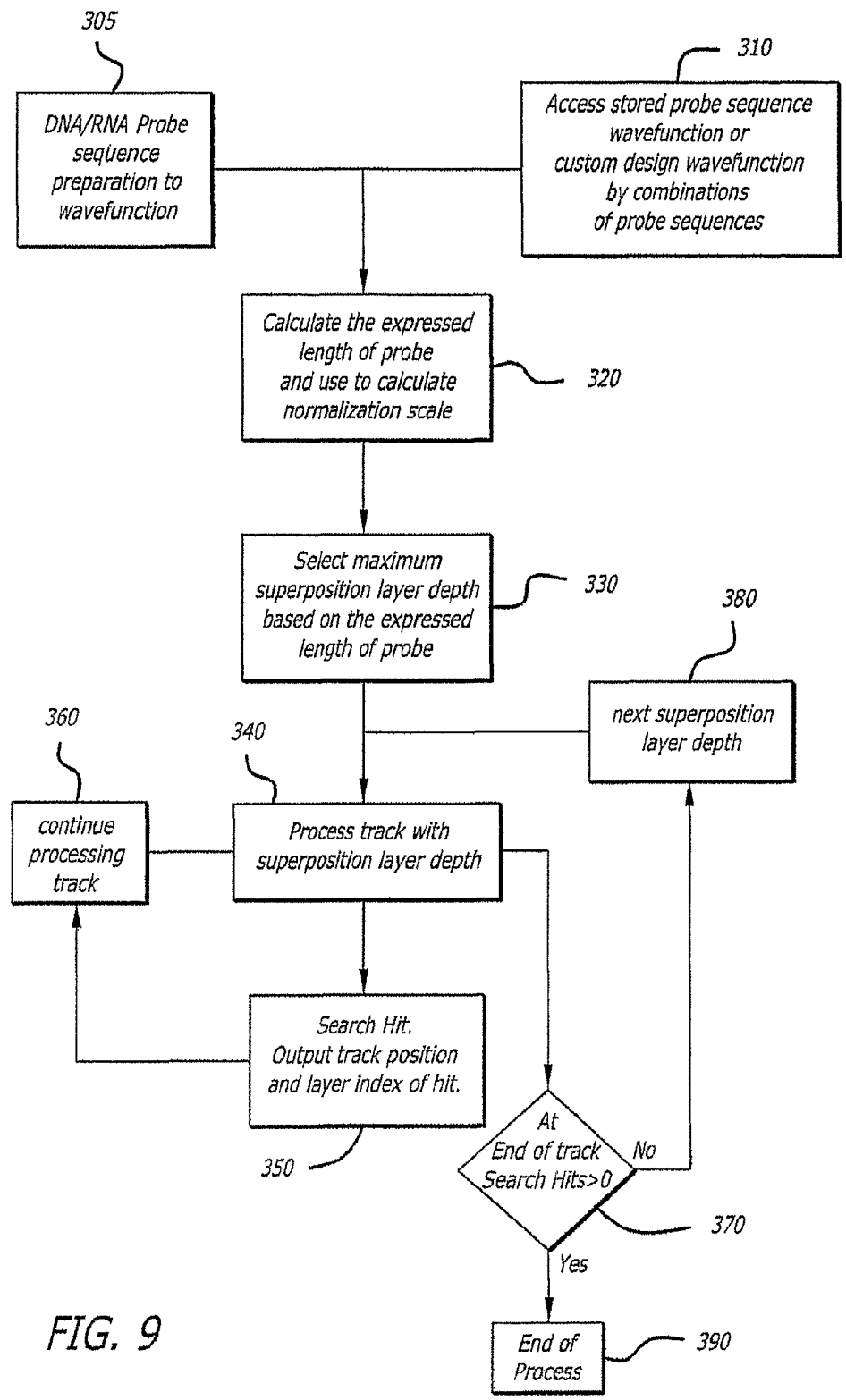
FIG. 9 illustrates the selection of a track from the multi-resolution database, the searching for hits in the selected track, and the selection of a next track for searching, according to an exemplary embodiment of the present disclosure.

FIG. 9 illustrates the selection of a track 902 from multi-resolution database 900, the searching for hits in the selected track, and the selection of a next track 902 at a different resolution for continued searching. A DNA/RNA probe sequence is prepared in step 305 by transforming to wavefunction form as discussed above. Alternatively, in step 310, a previously prepared probe sequence wavefunction may be obtained from storage (e.g., memory) for use, or combinations of probe sequences may be used to prepare customized wavefunctions for particular applications.

The probe sequence selected for use is passed to step 320, in which the expressed length of the probe is calculated. The expressed probe length is used to calculate the normalization scale factor applied during the searching process discussed above in modulus and normalization steps 122 and 140. Normalization is desired to attempt to make the output correlation peaks independent of the probe length.

In step 330, the maximum superposition layer depth is selected based on the expressed length of probe from step 320. In step 340, a track 902 is selected from multi-resolution database 900 corresponding to the maximum superposition layer depth that may be efficiently processed for the effective length of the probe. Then, a search as described above in FIG. 5 for method 100 is performed.

In step 350, a search hit (e.g., an R, S Hit Pair) from executing method 100 is output with its track position and the layer index of the hit. Processing of the track continues in step 360 to determine if additional search hits will be found. For example, anywhere from one to millions of hits may be found from the search of the first selected track 902.

In step 370, if the process is at the end of the selected track and at least one search hit has been found, then the process ends in step 390. If no search hits were found, then in step 380 another superposition layer depth is selected (e.g., half the layer depth just used in the failed search), and the corresponding track 902 is obtained from database 900 for additional processing using method 100 at step 340.

Figure 10:
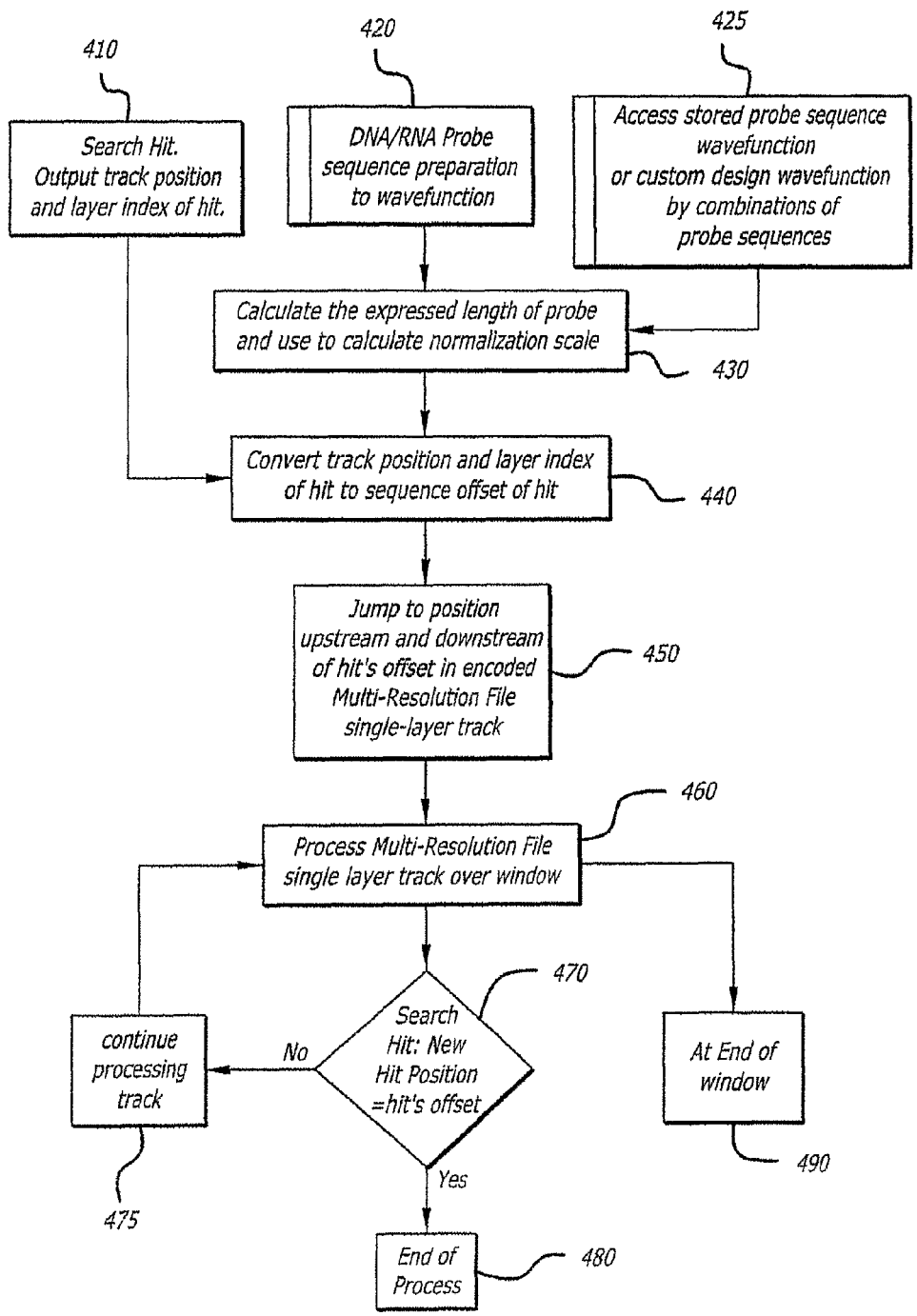
FIG. 10 illustrates the use of a single-layer track in the multi-resolution database to confirm a search hit located from the prior searching of one of several multiple-layer tracks in the multi-resolution database according to an exemplary embodiment of the present disclosure.

FIG. 10 illustrates the use of a single-layer track in the multi-resolution database to confirm one or more search hits located from one of several multiple-layer tracks 902 in the multi-resolution database 900. A probe input is selected in steps 420 and 425 are similar to steps 305 and 310 discussed above, and a probe length is determined in step 430 similarly as discussed above in step 320. In step 410, the one or more search hits from step 350 are used as an input to step 440.

In step 440, the track position and layer index of each incoming search hit are converted to a target sequence offset. In other words, the track position can be converted to a sequence offset of the hit within the original input sequence. As discussed above, in step 182 the layer index may be converted to a target section number. The track position may then be calculated as the count of frames from the track start plus the length of a single target section times the target section number.

In step 450, the process determines a position in the target sequence that is upstream of the search hit's offset in the single-layer track 902 (e.g., Track 6 of FIG. 6) of the multi-resolution database 900. Step 450 is performed to attempt to confirm that a hit actually exists in the original target location identified from the search of method 100.

Simply stated, a separate process is started for each potential search hit that is generated from method 100 of FIG. 5. A search hit is processed again over a range (referred to below as a "window") bounded by a small positional distance upstream from the search hit's position in the target sequence to a small positional distance downstream (e.g., this may be just a couple of frames). Each search hit may be confirmed by checking the single-layer track of database 900 (note that there is no superposition in the single-layer track). It should be noted that in the single-layer track of database 900, dual R, S data is not needed. This is so because, if the separation between the R and S data is twice the layer index and layer index zero is being used, then the R and S data are identical and only the R or S data is needed.

In step 460, the single-layer track is processed over the window that is determined by the primary frame that contains the position of the hit, plus an additional downstream (successor) frame if the position within the frame is such that part of the matching sequence is in that downstream frame. In addition it may be desirable to start processing with the frame that is immediately upstream (preceding) the frame that contains the hit in order to provide an overlap frame at steps 116 and 134 that will be combined via steps 118 and 136 with the primary frame that contains the position of the hit. The prepared probe sequence from step 420 or 425 is used here again, in addition to the search that generated the search hit, because the interference process is basically being repeated on the single-layer track as a confirmation of the search hit.

In step 470, if the hit position determined from the single-layer track is equal to the input search hit position, then the process ends at step 480. If the hit position is not equal to the input position, then in step 475 the single-layer track is processed further. If the hit position is upstream (preceding) the input position, processing will continue until the input position has been reached and passed. The processing of a single wavefunction frame will yield a full N potential match alignments, so even the minimum window equal to a single frame will detect all the potentially multiple match alignments that may be present in the target sequence information inside this window. In this way, all of the multiple hits will be detected based even a single hit occurring an a superposition layer interference as in method 100. Processing of the single-layer track continues until the end of the window being processed is reached at step 490.

Search Output Display

Another aspect of the present disclosure is a method for presenting search results to a user. More specifically, the output may be presented to a user as a graph or other visual representation to illustrate the results of the search using a particular probe. This output may be presented, for example, on user display 205. This visual representation also may dynamically change its appearance to show correlations, their strengths and phases as output from method 100 or in the hit confirmation processing step 450. The normalized magnitude calculated in steps 122 and 140 may be represented as the height of a graph (e.g., the y-axis) at any point along a sequence position axis (e.g., the x-axis). Where multiple hits occur, the height of the graph may represent the count of matches within an arbitrary length frame or sliding window (e.g., histogram frequencies rather than individual matches).

The graph may, for example, display peaks of various heights for which the height is a quantitative measure of the binding energy between probe and its matching sequence in the target. The peaks may be positioned along an axis containing the target sequence. For example, either a similarity match or a double-stranded complementary base pairing match may be selected (for either DNA or RNA).

Each peak may further be coded with different colors to indicate the phase of the match. For example, a red color may be used to highlight strong in-phase matches so that red peaks are the most significant features in the visual display.

Additional information regarding the providing of visual representations to a user of the output search results is provided in APPENDIX A to this application, which is hereby fully incorporated by reference herein.

Custom Search Service Example

The following is a non-limiting example of a custom search service that may be provided using the present disclosure. A user provides target and probe information for processing using the above system and method. The information, results, and service may be communicated and provided using an application service provider (ASP) business model over, for example, the Internet.

The user designs one or more probes according to the following typical design rules: The total probe length is between 5 and 2,048 bases. Each base position may be individually specified to be one of A, C, T, or G, or each position may be specified to contain a blend of two different bases, for example a purine base hybrid that represents either adenine or guanine, or a pyrimidine base hybrid that represents either cytosine or thymine.

Each base may be individually weighted to be more or less significant by a factor $\gamma_k$ specifying the overall weight given to that base position, where k is the individual base position starting at index 0. The default $\gamma_k$ is set to 100%.

For example, to program a gene probe comprising a number of expressed exons, plus promoters and regulatory binding sites with non-coding bases between them, the exonic, promoter and regulatory sequences would be represented with different $\gamma_k$ values. For instance, evolutionarily-conserved base positions and known functional patterns may be given accordingly greater $Y_k$ values. As another example, protein coding frames may be designed giving greater weight to the first and second base positions in each codon in a mRNA translation reading frame, and proportionally less weight given to the third base positions (since these may not affect amino acid coding of the triplet), since all base triplet codon patterns can be expressed using $\gamma_k$. A pattern of absolute gaps may be formed by setting $\gamma_k$ to zero.

The probes are processed against the desired chromosome and genome targets, then the results are provided to the user. This may be a map that includes the position of direct hits and close homologies of the probe in the target DNA. Both matching and complementary sequences may be detected equally. Furthermore, hits may be ranked according to a distance metric representing the total base pair match/mismatch enthalpy calculated at single base pair resolution.

Applications

The system and method of the present disclosure are useful in a wide variety of data storage and searching applications such as, for example, surveying short sequences involved in gene regulation. The present disclosure may be applied to providing an "in silico" assay that has single base resolution to serve DNA primer design and screening, a need that is common to all DNA amplification bio-assays using the Polymerase Chain Reaction (PCR).

Additional applications include the following areas: screening oligonucleotide sequences for their ability to selectively bind desired target sites and not bind other undesired sites (this screening may be useful in siRNA gene silencing to safely and selectively turn off genes based on designer oligonucleotides); accelerating the drug discovery cycle by replacing complex and expensive wet laboratory tests with faster software tools using the system and method disclosed herein; screening for specificity of genetically engineered zinc finger DNA binding proteins and related designed endonucleases, and mapping of (micro RNA) miRNA complementary sites within genes and transcribed DNA, as potential gene regulation sequences.

It will be apparent from the foregoing that the wavefunctions as described possess a desirable property as contrasted to conventional database data encoding in that it achieves delocalized distribution of individual data items in such a way that is robust even in the presence of multiple point errors. This aspect of the method may be exploited by using analog or digital media and functional processing methodologies that are lower cost due to a tolerance of defects and noise as compared against, for example, higher-cost defect-free media and noise-free functional processing methodologies.

It will also be apparent from the foregoing that various steps in the method including unitary orthogonal transform and its inverse, and the interference of multiple wavefunction may each be realized in an optical system. Such functional implementation may proceed to the extent that the microprocessor component in the system may become non-essential, for example, if all steps are performed by dedicated optical hardware.

Yet other applications of the present disclosure are in the associative memory, quantum computing, and other fields and include the following applications: coding and decoding data for wideband communications, database search, biometrics, network routing optimization, free energy dynamics, universal sensor archival search and storage, financial market analysis, and retail data mining.

The system and method described herein may be used to provide a quantum memory component to perform an associative memory pattern matching function, and that may be logically extended by adding further quantum processing and algorithm components around the quantum memory core to build a quantum computer. Such a quantum computer may use photonic hardware and be based on laser optics.

Conclusion

As previously stated, the disclosure is not limited to searching of DNA/RNA sequences and while the foregoing description was made in this specific context, the disclosure can be utilized in many other application areas, including, but not limited to, other types of pattern recognition and data searching processes and the other areas discussed above.

Additionally, it can be readily understood that the foregoing processes can be embodied in a computer program that is executed by computer hardware that includes one or more processors for executing the computer program or other hardware variations mentioned above. The computer program can be stored on any type of recording medium such as a magnetic drive, floppy disk, tape drive, CD-ROM, flash memory, etc. and the disclosure is not limited to any particular type of recording medium or computer hardware.

By the foregoing disclosure, an improved system and method for a storing and searching large data sets (e.g., stored in a database) have been described. Although specific exemplary systems and methods were described above, one of skill in the art will recognize that in other embodiments many of the above steps may be re-arranged and/or omitted. The foregoing description of specific embodiments reveals the general nature of the disclosure sufficiently that others can, by applying current knowledge, readily modify and/or adapt it for various applications without departing from the generic concept. Therefore, such adaptations and modifications are within the meaning and range of equivalents of the disclosed embodiments. The phraseology or terminology employed herein is for the purpose of description and not of limitation.

Appendix A

A visual output display method is described here as an example of how DNA and RNA search results may be presented to a user. Search output results have traditionally been text-based showing, for example, the probe sequence aligned to a matching target sequence, together with some location information such as a chromosome position index. These text results are useful for close examination of matches that are output from the search. However, they have several limitations when used alone.

First, there is the problem of "not seeing the wood for the trees." In other words, there can be so much data that the overall patterns are not seen by the user. For shorter probes, such as lengths of twelve bases or less, the number of hits increases dramatically, so that there may be thousands of sequences output that match the probe. As a result of the large volume of matches, text output becomes overwhelming and confusing to the user. Second, traditional text output is not interactive in a way that easily allows a user to browse over the data set changing scope and focus according to their point of interest.

To overcome these limitations of text-based outputs, search results may be displayed as color-coded peaks on a three-dimensional virtual chromosome image. The position of this peak will correspond to the location of the match. Genes may be displayed as solid blocks so that it is apparent visually if a peak is located within a gene or outside it. The relative height of the peak may indicate the strength of the match, with 100% matches appearing as taller peaks than partial matches.

Alternatively, when there are a larger number of matches, the peak height may correspond to histogram frequency showing match density within a region, rather than single matches. Multiple different probe channels may be displayed as parallel tracks on a three-dimensional virtual chromosome. In this way, the results of multiple different searches may be compared at a glance across the entire chromosome. The use of multiple probe channels in the display can reveal subtle dependencies and relationships between different sequence elements.

One advantage of a 3D display or model is that the user can select a viewpoint to focus on an area of special interest in a sequence. The viewpoint may be controlled in real-time by, for example, mouse clicks or movements so that the virtual reality experience is enhanced. For example, dragging a mouse left button across the screen or up-and-down may rotate the 3D model, allowing the user to view it from any angle.

Similarly, dragging a mouse right button across the screen or up and down may move the 3D model as a translation in space. The user may also zoom in to get a close up view of a part of the model or zoom out to see the entire chromosome using, for example, middle and right button mouse clicks. As the user's viewpoint zooms in closer to the chromosome, additional information may be displayed around the color-coded peaks or gene blocks. This may be alphanumeric information such as, for example, a chromosome position, base sequence or gene label.

As shown in the screen shots attached below, the probe and matching target sequence may be displayed as three-dimensional text strings. This allows a mixed display containing both color-coded peaks and textual information in the same view. The textual and graphical information may include hypertext links, for example, to external data sources, programs, and Internet resources.

A separate user interface (e.g., control box) may also be provided showing which probes are displayed on the virtual chromosome and their color coding. Slider controls may also be used to control the scaling of the display peaks and position of text labels. Buttons may provide additional interactive display options for each probe channel.

The visual output display method above may be implemented on conventional computer hardware systems using any of a number of software languages.

The invention claimed is:

1. A method implemented using a computer for parallel searching for a probe in a multi-resolution database comprising stored information, the method comprising:
    obtaining the multi-resolution database;
    performing, at the computer, orthogonal domain unitary encoding of the stored information to a vector in an orthogonal basis to generate a plurality of wavefunctions, wherein each respective wavefunction in the plurality of wavefunctions corresponds to a different portion of the stored information;
    forming a plurality of superposition wavefunction representations, wherein each of the plurality of superposition wavefunction representations is a superposition of the plurality of wavefunctions, whereby the plurality of wavefunctions are additively combined to create the superposition wavefunction representation, and wherein each respective superposition wavefunction representation in the plurality of superposition wavefunction representations (i) represents all or a portion of the stored information and (ii) comprises a plurality of layers;
    encoding the probe as one or more wavefunctions; and
    permitting interference between a probe wavefunction and one or more of the plurality of superposition wavefunction representations thereby searching for the probe by identifying a match between the probe and a portion of the stored information as represented by the plurality of superposition wavefunction representations, wherein, when a match is found, the portion of the stored information responsible for the match is identified by an index to a layer, and an offset within the layer, in the plurality of layers in a superposition wavefunction representation in the plurality of superposition wavefunction representations where a representation of the stored information responsible for the match is located.

2. The method of claim 1 wherein the stored information comprises a DNA or RNA sequence.

3. The method of claim 2 wherein the parallel searching comprises searching to match the probe to the DNA or RNA sequence.

4. The method of claim 1 further comprising:
    encoding the information into a complex orthogonal encoding basis to provide a plurality of complex numbers; and
    transforming the plurality of complex numbers into the plurality of superposition wavefunction representations.

5. The method of claim 4 wherein the information comprises real number data.

6. The method of claim 4 wherein the information comprises complex number data.

7. The method of claim 4 wherein:
    the information comprises a plurality of real or complex numbers;
    each of the plurality of real or complex numbers is encoded with the position of a delta function on an arbitrary number line to provide a plurality of encoded real or complex numbers; and
    the plurality of wavefunctions are derived from the plurality of encoded real or complex numbers.

8. The method of claim 1 wherein the orthogonal domain unitary encoding is a Fourier transform.

9. The method of claim 1, wherein the probe is individually weighted.

10. A computer system for searching for a probe in a multi-resolution database having stored information, the system comprising:
    a processor;
    a memory, the memory storing the multi-resolution database and configured to store a set of instructions, which when executed by the processor cause the computer system to perform a method, the method including:
    performing orthogonal domain unitary encoding of the stored information to a vector in an orthogonal basis to generate a plurality of wavefunctions, wherein each respective wavefunction in the plurality of wavefunctions corresponds to a different portion of the stored information;
    forming a plurality of superposition wavefunction representations, wherein each of the plurality of superposition wavefunction representations is a superposition of the plurality of wavefunctions, whereby the plurality of wavefunctions are additively combined to create the superposition wavefunction representation, and wherein each respective superposition wavefunction representation in the plurality of superposition wavefunction representations (i) represents all or a portion of the stored information and (ii) comprises a plurality of layers; and
    encoding the probe as one or more wavefunctions; and
    permitting interference between a probe wavefunction and one or more of the plurality of superposition wavefunction representations thereby searching for the probe by identifying a match between the probe and a portion of the stored information as represented by the plurality of superposition wavefunction representations, wherein, when a match is found, the portion of the stored information responsible for the match is identified by an index to a layer, and an offset within the layer, in the plurality of layers in a superposition wavefunction representation in the plurality of superposition wavefunction representations where a representation of the stored information responsible for the match is located.

* * * * *